United States Patent [19]
Boyd et al.

[11] Patent Number: 5,455,251
[45] Date of Patent: Oct. 3, 1995

[54] MICHELLAMINE ANTIVIRAL AGENTS, COMPOSITIONS, AND TREATMENT METHODS

[75] Inventors: Michael R. Boyd, Ijamsville; John H. Cardellina, II, Walkersville; Kirk P. Manfredi, Frederick, all of Md.; John W. Blunt, Christchurch, New Zealand; Lewis K. Pannell, Silver Spring, Md.; James B. McMahon; Robert J. Gulakowski, both of Frederick, Md.; Gordon M. Cragg, Bethesda, Md.; Gerhard Bringmann, Wurzburg, Germany; Duncan Thomas, Corvallis, Oreg.; Johnson Jato, Yaounde, Cambodia

[73] Assignee: The United States of America as represented by the Secretary of the Department of Health and Human Services, Washington, D.C.

[21] Appl. No.: 49,824

[22] Filed: Apr. 19, 1993

Related U.S. Application Data

[63] Continuation-in-part of Ser. No. 684,197, Apr. 12, 1991, abandoned.

[51] Int. Cl.⁶ .......................... A61K 31/47; C07D 401/10
[52] U.S. Cl. ............................................. 514/308; 546/140
[58] Field of Search .............................. 546/140; 514/308

[56] References Cited

U.S. PATENT DOCUMENTS 3,751,419  8/1973  Ziegler .................................. 546/140

FOREIGN PATENT DOCUMENTS

WO92/18125  10/1992  WIPO .................................. 546/140

OTHER PUBLICATIONS

Stuart–Harris, "The Background to Chemotherapy of Virus Diseases", 1965, pp. 76–77.
Manfredi et al. *J. Med. Chem*, vol. 34, No. 12, 1991, pp. 3402–3405.
Ruangrungsi, et al, *J. Natural Products* vol. 48, No. 4, 1985, pp. 529–535.
Sandstrom, Drugs, vol. 34, 1987 pp. 373–390.
Bringmann, "The Naphthyl Isoquinoline Alkaloids," *The Alkaloids*, vol. 29, Brossi, ed., Academic Press, New York 141–184 (1986).
Bringmann et al., *Planta Med.*, 58 (Suppl. 1), 703–704 (1992).
Gustafson et al., "AIDS–Antiviral Sulfolipids from Cyanobacteria (Blue–Green Algae)," *J. National Cancer Institute*, 81 (16) (Aug. 16, 1989).
Weislow et al., "New Soluble–Formazan Assay for HIV–1 Cytopathic Effects: Application to High-Flux Screening of Synthetic and Natural Products for AIDS–Antiviral Activity," *J. National Cancer Institute*, 81 (8), 577–586 (Apr. 19, 1989).

*Primary Examiner*—Bernard Dentz
*Assistant Examiner*—Zinna N. Davis
*Attorney, Agent, or Firm*—Leydig, Voit & Mayer, Ltd.

[57] ABSTRACT

The present invention provides new antiviral compounds, i.e., michellamines and derivatives and pharmacologically acceptable salts thereof, methods for isolating such antiviral compounds from a plant species of the genus Ancistrocladus, antiviral compositions containing such antiviral compounds, and methods of using such antiviral compounds for treating patients with viral infections. The antiviral compounds of the present invention inhibit the reproduction and cytopathicity of human acquired immunodeficiency viruses.

36 Claims, 13 Drawing Sheets

MICHELLAMINE A

MICHELLAMINE B

MICHELLAMINE C

MICHELLAMINE ANTIVIRAL AGENTS, COMPOSITIONS, AND TREATMENT METHODS

This application is a continuation-in-part of Ser. No. 07/684,197 filed Apr. 12, 1991, now abandoned.

TECHNICAL FIELD OF THE INVENTION

The present invention relates to compounds which exhibit antiviral activity, compositions containing the compounds, methods for isolating the compounds from plants, and methods for using the compounds. The compounds of the present invention exhibit advantageous pharmacological, toxicological, and antiviral properties, such as, for example, the inhibition of the cytopathic effects of the human immunodeficiency virus (HIV), which is implicated as a causative agent of Acquired Immune Deficiency Syndrome (AIDS).

BACKGROUND OF THE INVENTION

AZT is the first commercially available, known clinically active agent currently used widely in the therapy of AIDS. While extremely useful in antiviral therapy, AZT is limited in its use due to its toxicity and an insufficient therapeutic index to make it adequate for therapy. Thus, new classes of antiviral agents to be used alone or in combination with AZT and other agents are needed urgently for effective antiviral therapy against HIV. It is also especially important to have new agents which have antiviral activity against HIV-1 as well as HIV-2.

It is an object of the present invention to provide such new antiviral agents. It is a further object of the present invention to provide methods of obtaining such antiviral agents, pharmaceutical compositions containing such antiviral agents, and methods of using such antiviral agents.

These and other objects and advantages of the present invention, as well as additional inventive features, will be apparent from the description of the invention provided herein.

BRIEF SUMMARY OF THE INVENTION

The present invention is directed specifically to a substantially pure compound having the formula:

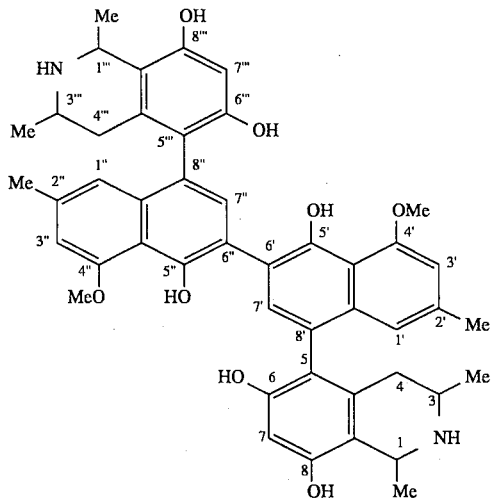

or a pharmacologically acceptable salt thereof, particularly a substantially pure compound having the formula:

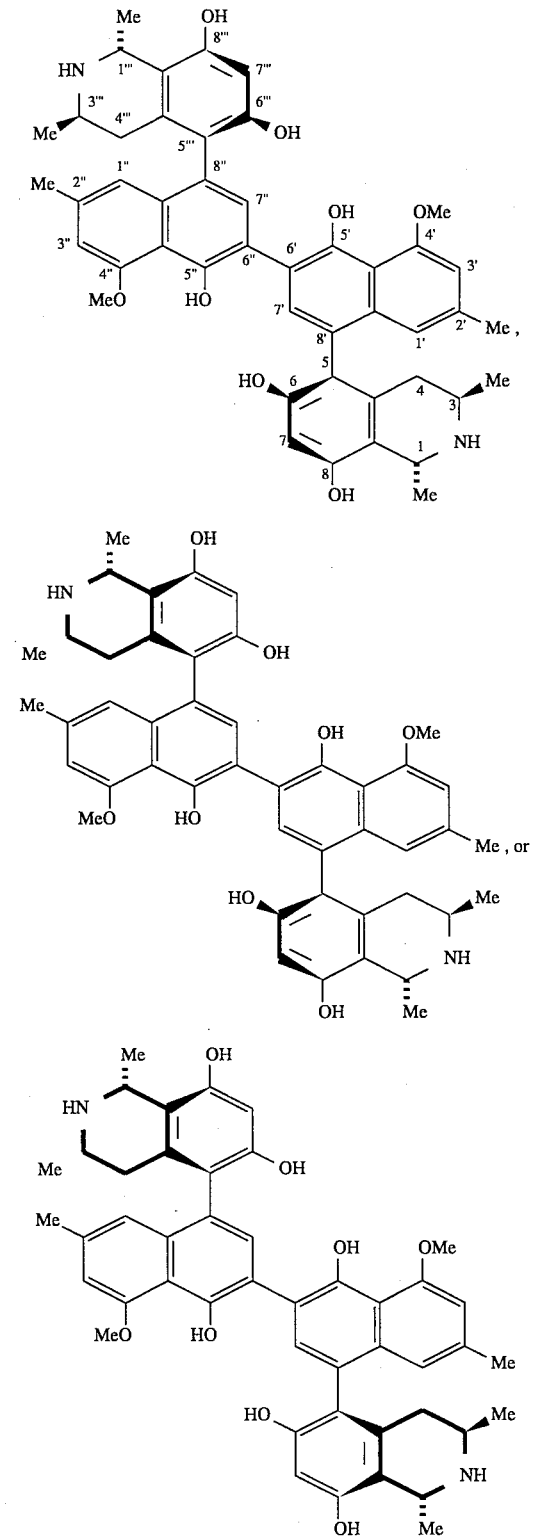

or a pharmacologically acceptable salt thereof. These compounds are hereinafter referred to as michellamines, in particular michellamines A, B, and C, respectively.

The present invention is also directed more generally to a substantially pure michellamine or derivative thereof having the formula:

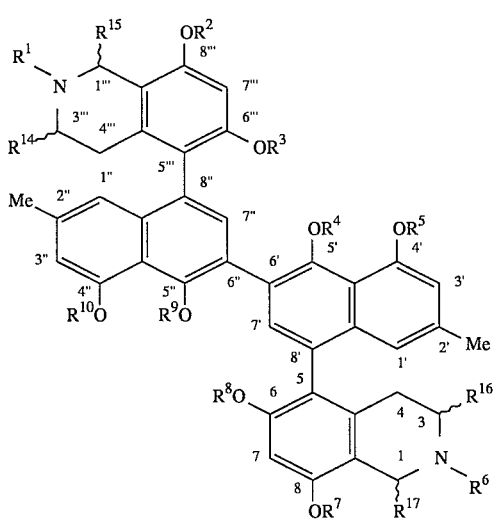

or a pharmacologically acceptable salt thereof, particularly a substantially pure compound having the formula:

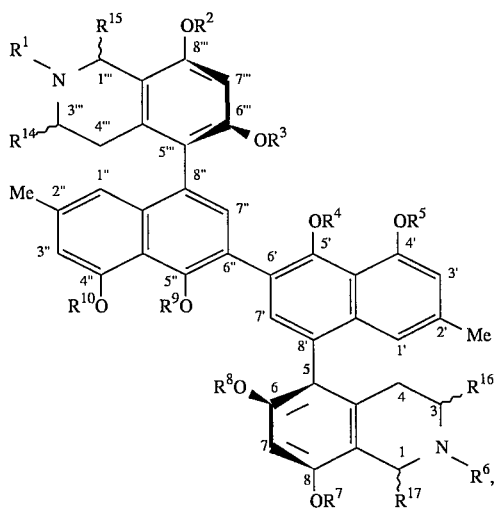

or

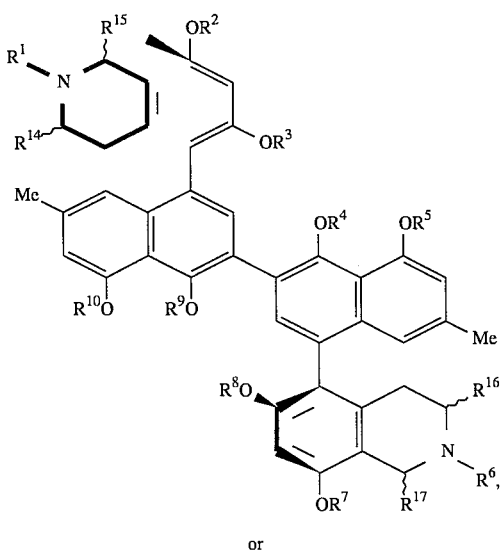

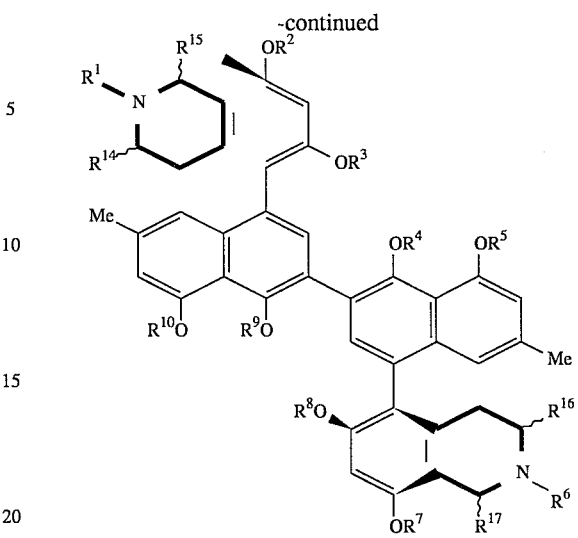

wherein $R^1$ and $R^6$ are the same or different and are each H, $C_1-C_6$ alkyl, $R^{11}CO-$, or $R^{11}SO_2-$ wherein $R^{11}$ is $C_1-C_6$ alkyl or aryl;

$R^2, R^3, R^4, R^7, R^8$ and $R^9$ are the same or different and are each H, $C_1-C_6$ alkyl, $R^{11}CO-$, $R^{11}SO_2-$ wherein $R^{11}$ is defined above;

$R^5$ and $R^{10}$ are the same or different and are each H, $C_1-C_6$ alkyl,

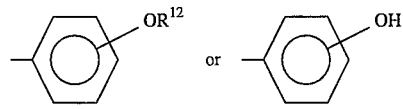

wherein $R^{12}$ is $C_1-C_6$ alkyl or $R^{13}CO-$ or $R^{13}SO_2-$, wherein $R^{13}$ is $C_1-C_6$ alkyl or aryl;

$R^{14}, R^{15}, R^{16}$, and $R^{17}$ are the same or different and are each

◂CH₃ or ⋯CH₃;

and wherein one or more of the ring H positions at 1', 3', 7', 4, 7, 1", 3", 7", 4''' and 7'''can be substituted with a halogen, nitro, amino, hydroxyl, thiol, or cyano group; or a pharmacologically acceptable salt thereof.

The present invention further provides a method of isolating the aforementioned michellamines from a new species of the plant genus Ancistrocladus, tentatively named *Ancistrocladus sp. novum* (DT 6889), which comprises the steps of:

(a) extracting dried plant material with an organic solvent to obtain a crude extract;

(b) acid-base partitioning said crude extract to obtain a crude organic base fraction;

(c) subjecting said crude organic base fraction to centrifugal partition chromatography; and (d) isolating said michellamines with an amine-bonded phase HPLC column.

The present invention also provides a method for the interconversion of either of michellamines A or B, into a mixture of michellamines A, B, and C, which comprises:

(a) dissolving either of michellamines A or B in an organic solvent; and (b) reacting said michellamines A or B with a base.

The present invention includes the aforementioned michellamines, particularly michellamines A, B, and C, their derivatives, and pharmacologically acceptable salts thereof in substantially pure form, as well as antiviral compositions which comprise an antiviral effective amount of at least one of these michellamines, or derivatives or pharmacologically acceptable salts thereof, and a pharmacologically acceptable carrier. The antiviral compositions can further include an antiviral effective amount of AZT and/or other known antiviral agents.

The present invention also encompasses a method of treating a viral infection which comprises administering to a patient in need thereof an antiviral effective amount of at least one of these michellamines, particularly michellamines A, B, or C, or a derivative or pharmacologically acceptable salt thereof. The method of the present invention may also involve co-administering an antiviral effective amount of AZT and/or other known antiviral agents with at least one of these michellamines or a derivative or pharmacologically acceptable salt thereof.

BRIEF DESCRIPTION OF THE DRAWINGS

FIGS. 2A, 2B, and 2C show the effects of a range of concentrations of michellamine A upon uninfected CEM-SS cells (o) and upon CEM-SS cells infected with HIV-1 (●), as determined after 6 days in culture. FIG. 2A depicts the relative numbers of viable CEM-SS cells, as assessed by the BCECF assay. FIG. 2B depicts the relative DNA content of the respective cultures. FIG. 2C depicts the relative numbers of viable CEM-SS cells, as assessed by the XTT assay. In FIGS. 2A, 2B, and 2C, the data points are represented as the percent of the uninfected, non-drug treated control values. FIG. 2D shows the effects of a range of concentrations of michellamine A upon indices of infectious virus or viral replication. These indices include viral reverse transcriptase activity (▲), production of viral core protein p24 (♦), and syncytium-forming units (■). In FIG. 2D, the data points are represented as the percent of the infected, non-drug treated control values.

FIGS. 3A, 3B, and 3C show the effects of a range of concentrations of michellamine A (HBr salt) upon uninfected CEM-SS cells (o) and upon CEM-SS cells infected with HIV-1 (●), as determined after 6 days in culture. FIG. 3A depicts the relative numbers of viable CEM-SS cells, as assessed by the BCECF assay. FIG. 3B depicts the relative DNA content of the respective cultures. FIG. 3C depicts the relative numbers of viable CEM-SS cells, as assessed by the XTT assay. In FIGS. 3A, 3B, and 3C, the data points are represented as the percent of the uninfected, non-drug treated control values. FIG. 3D shows the effects of a range of concentrations of michellamine A (HBr salt) upon indices of infectious virus or viral replication. These indices include viral reverse transcriptase activity (▲), production of viral core protein p24 (♦), and syncytium-forming units (■). In FIG. 3D, the data points are represented as the percent of the infected, non-drug treated control values.

FIGS. 4A, 4B, and 4C show the effects upon a range of concentrations of michellamine B upon uninfected CEM-SS cells (o) and upon CEM-SS cells infected with HIV-1 (●) as determined after 6 days in culture. FIG. 4A depicts the relative numbers of viable CEM-SS cells, as assessed by the BCECF assay. FIG. 4B depicts the relative DNA content of the respective cultures. FIG. 4C depicts the relative numbers of viable CEM-SS cells, as assessed by the XTT assay. FIG. 4D shows the effects of a range of concentrations of michellamine B upon indices of infectious virus or viral replication. These indices include viral reverse transcriptase activity (▲), production of viral core protein p24 (♦) and syncytium-forming units (■). In FIGS. 4A, 4B, and 4C, the data points are represented as the percent of the uninfected, non-drug treated control values. In FIG. 4D the data points are represented as the percent of the infected, non-drug treated control values.

FIGS. 5A, 5B, and 5C show the effects of a range of concentrations of michellamine B (HBr salt) upon uninfected CEM-SS cells (o) and upon CEM-SS cells infected with HIV-1 (●), as determined after 6 days in culture. FIG. 5A depicts the relative numbers of viable CEM-SS cells, as assessed by the BCECF assay. FIG. 5B depicts the relative DNA content of the respective cultures. FIG. 5C depicts the relative numbers of viable CEM-SS cells, as assessed by the XTT assay. FIG. 5D shows the effects of a range of concentrations of michellamine B (HBr salt) upon indices of infectious virus or viral replication. These indices include viral reverse transcriptase activity (▲), production of viral core protein p24 (♦), and syncytium-forming units (,). In FIGS. 5A, 5B, and 5C, the data points are represented as the percent of the uninfected, non-drug treated control values. In FIG. 5D, the data points are represented as the percent of the infected, non-drug treated control values.

FIG. 6A shows the effects of a range of concentrations of michellamine A (free base) upon uninfected MT-2 cells (o) and upon MT-2 cells infected with HIV-2 (●) as determined using the XTT assay after 6 days in culture. The open bars show the corresponding supernatant reverse transcriptase activities.

FIG. 6B shows the effects of a range of michellamine A (HBr salt) concentrations upon uninfected MT-2 cells (o) and upon MT-2 cells infected with HIV-2 (●) as determined using the XTT assay after 6 days in culture. The open bars show the corresponding reverse transcriptase activities. In both graphs, all data points are represented graphically as the percent of their respective controls.

FIG. 7A shows the effects of a range of concentrations of michellamine B (free base) upon uninfected MT-2 cells (o) and upon MT-2 cells infected with the NIH-DZ strain of HIV-2 (●) as determined using the XTT assay after 6 days in culture. The open bars show the corresponding supernatant reverse transcriptase activities. FIG. 7B shows the effects of a range of michellamine B (HBr salt) concentrations upon uninfected MT-2 cells (o) and upon MT-2 cells infected with HIV-2 (●) as determined using the XTT assay after 6 days in culture. The open bars show the corresponding supernatant reverse transcriptase activities. In both graphs, all data points are represented graphically as the percent of their respective controls.

DESCRIPTION OF THE PREFERRED EMBODIMENTS

The present invention is predicated on the discovery that compounds isolated from a previously unknown plant species of the genus Ancistrocladus, tentatively named *Ancistrocladus sp. novum* (DT 6889), have antiviral properties and are useful in antiviral treatments. In particular, the present invention provides michellamines in substantially pure form and derivatives thereof which exhibit antiviral activity, methods of isolating such michellamines from native plants, pharmaceutical compositions containing such michellamines, and methods of treating viral infections through the administration of such michellamines.

The specific michellamine of interest has the formula:

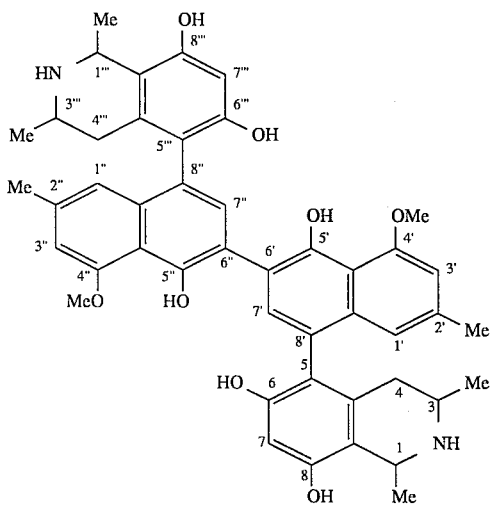

or is a pharmacologically acceptable salt thereof, and particularly is a compound of formula:

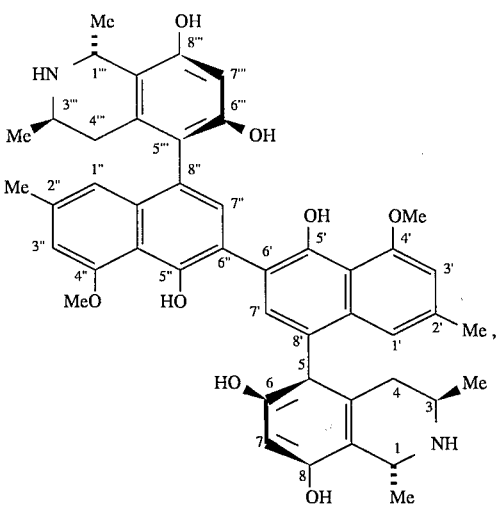

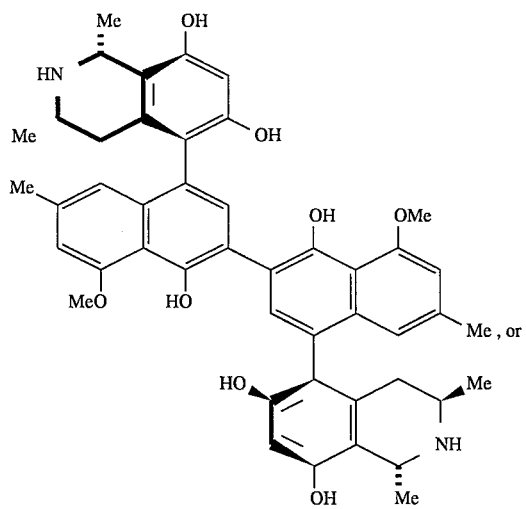

Figure 1A:
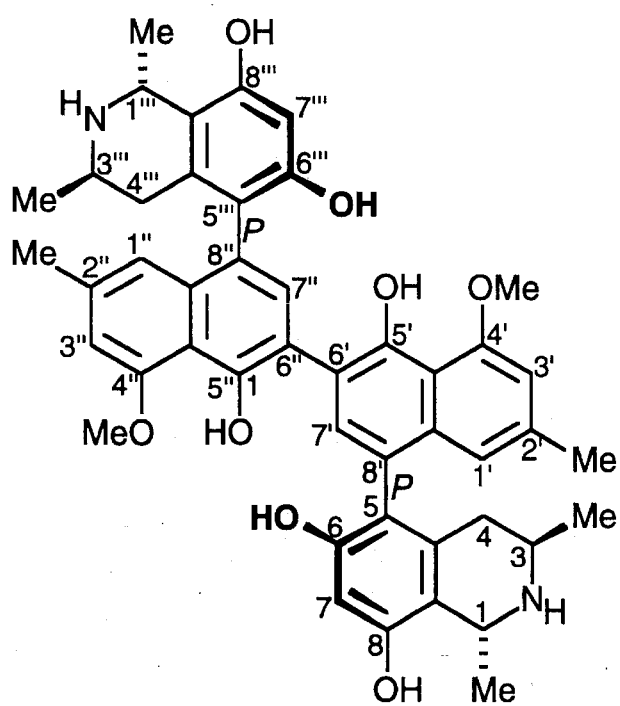
FIG. 1A–C illustrate the structures of michellamines A, B, and C, respectively. The ring-position numbering scheme is shown only for michellamine A, but is the same for michellamines B and C.
Figure 1B:
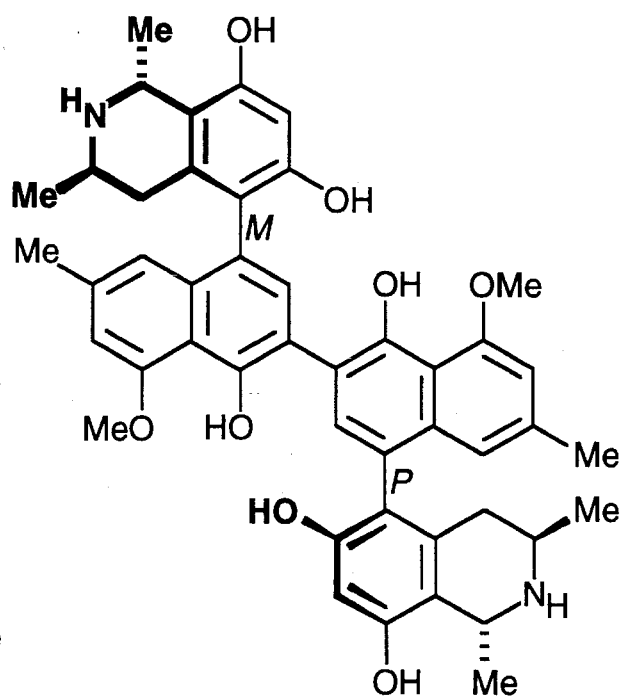
Figure 1C:
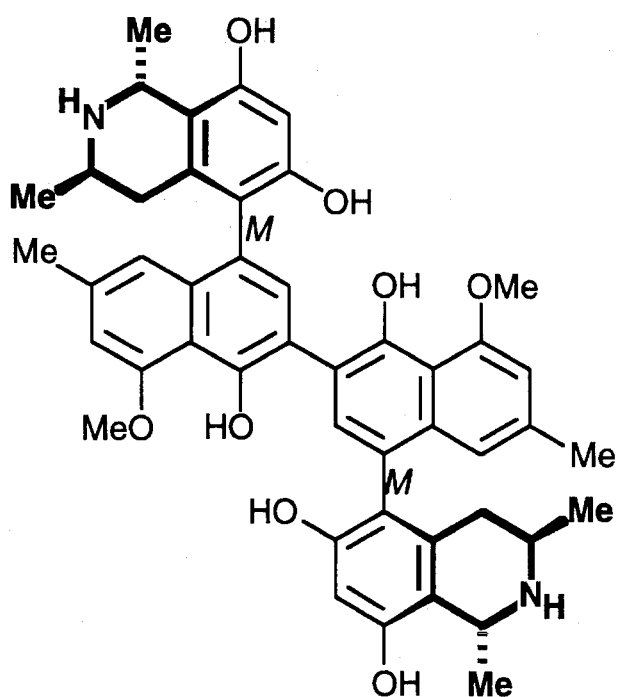
Figure 2A:
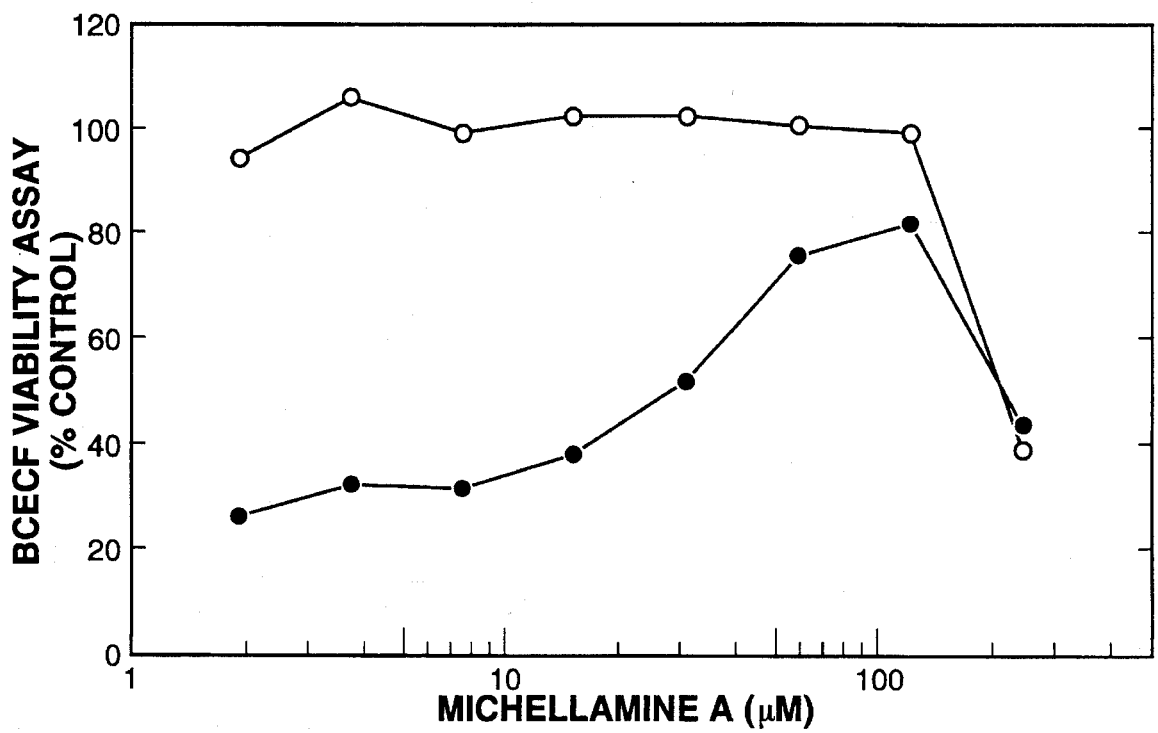
FIGS. 2A–D show the anti-HIV-1 activity of michellamine A (free base).
Figure 2B:
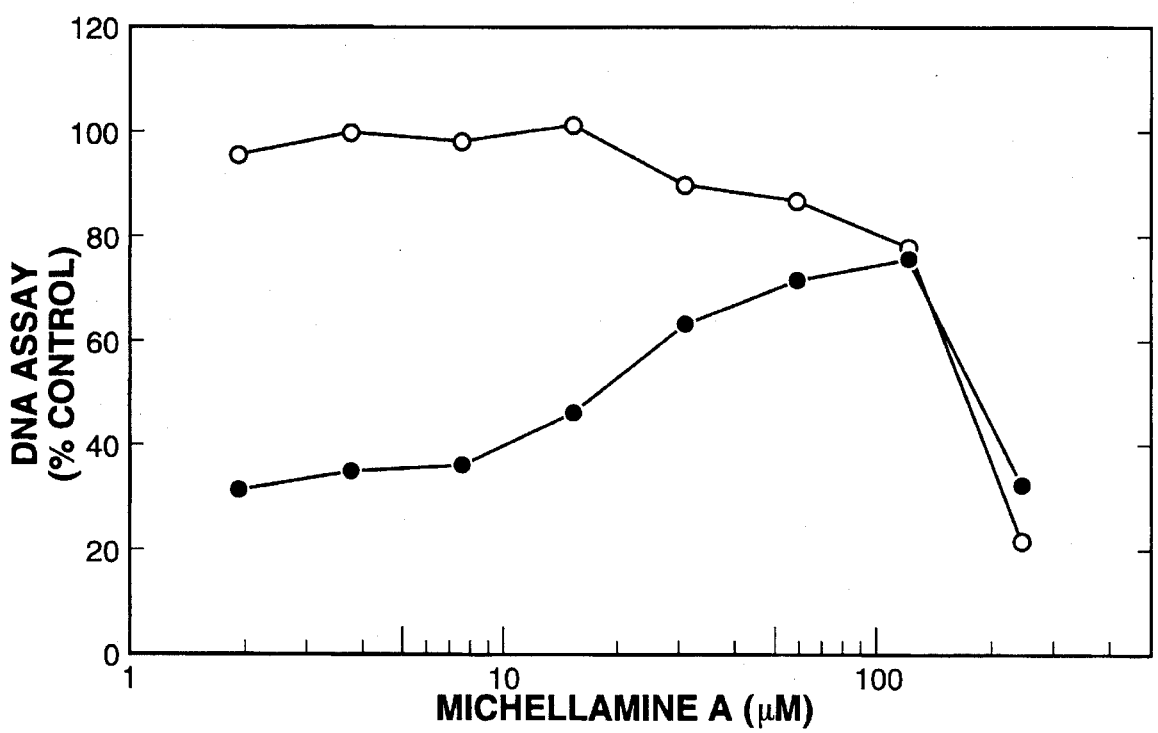
Figure 2C:
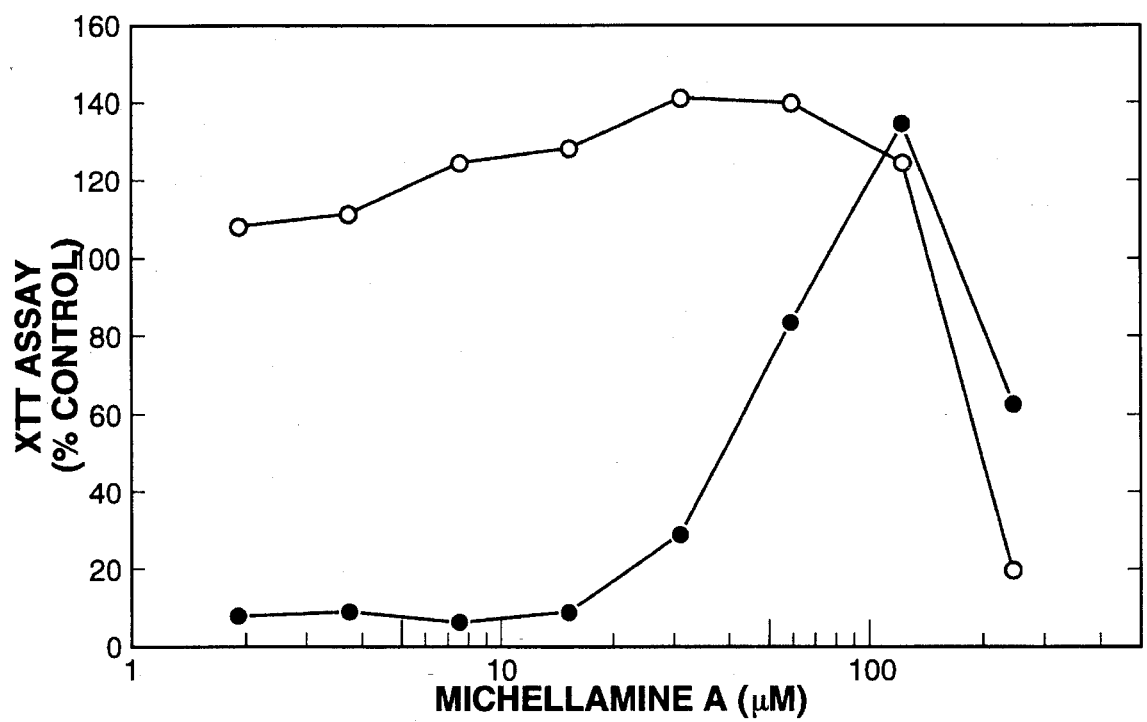
Figure 2D:
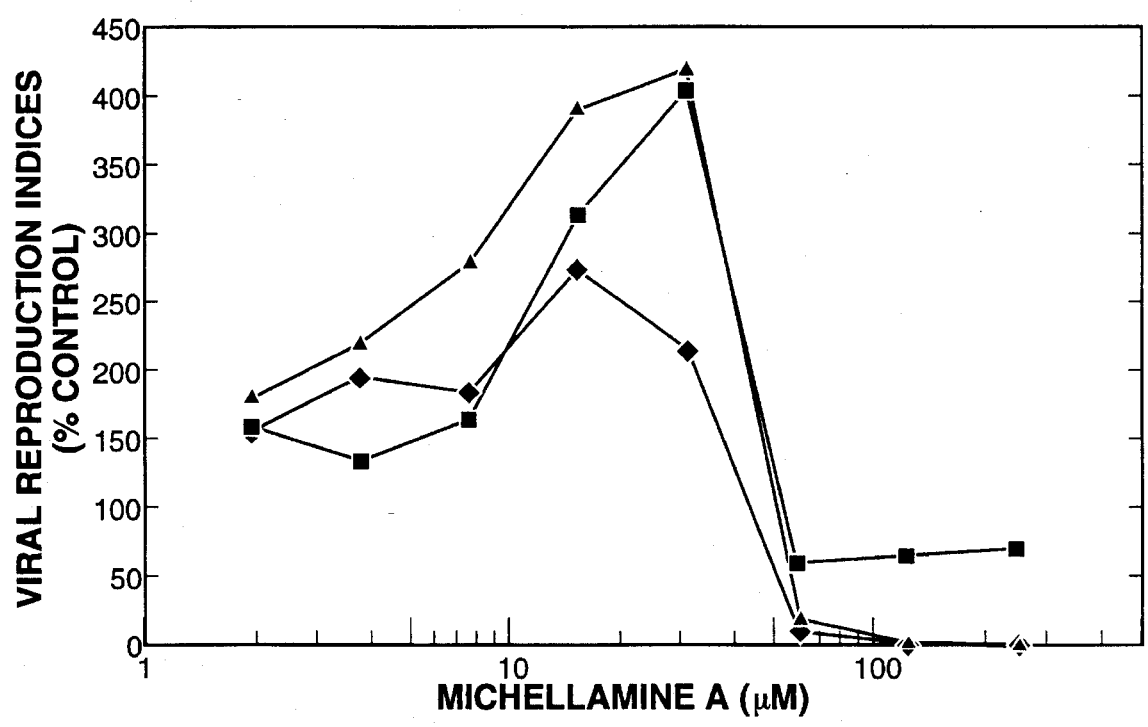
Figure 3A:
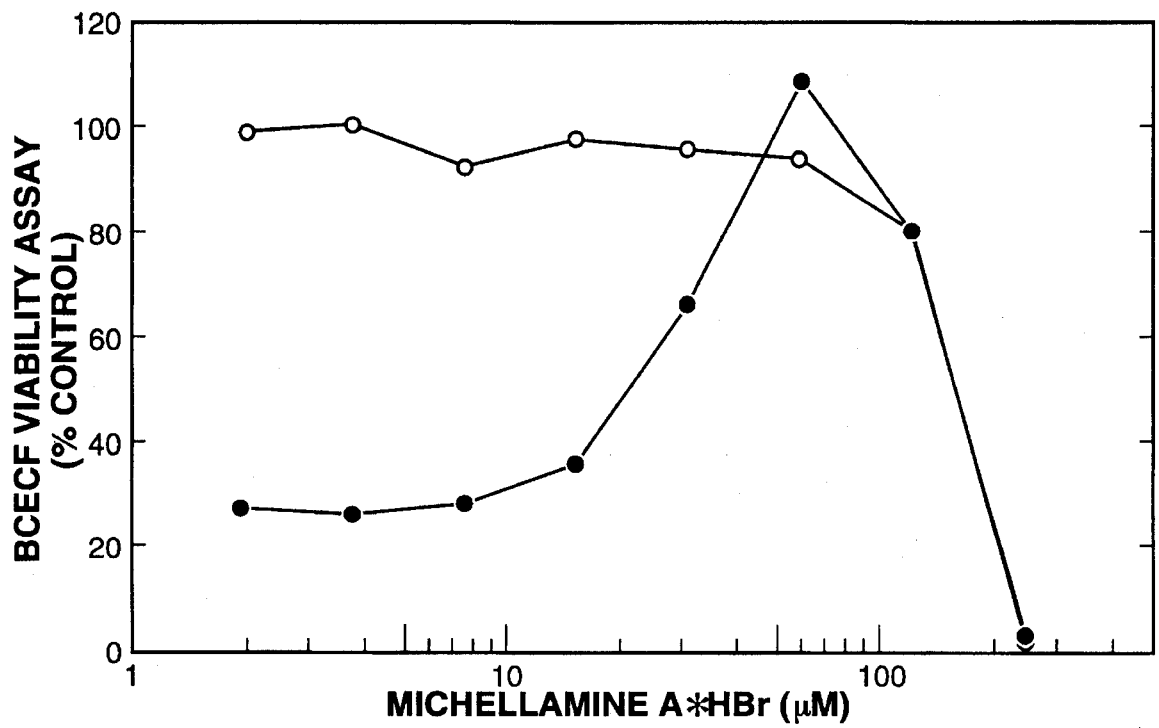
FIGS. 3A–D show the anti-HIV-1 activity of michellamine A (HBr salt).
Figure 3B:
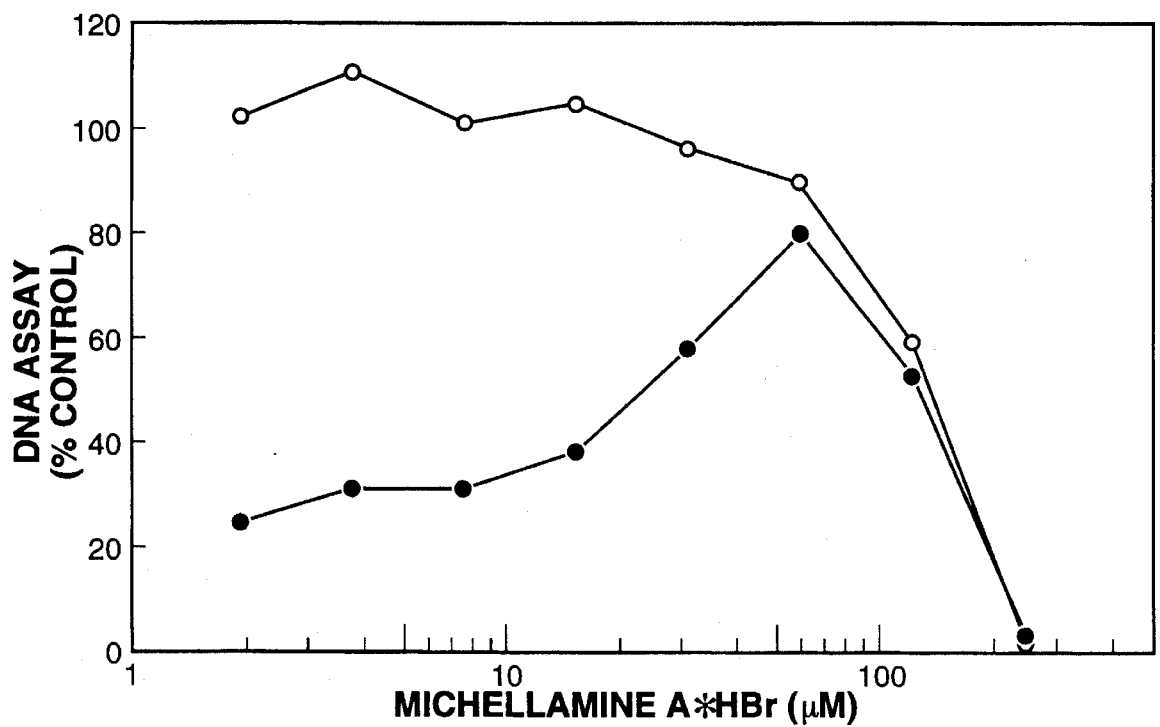
Figure 3C:
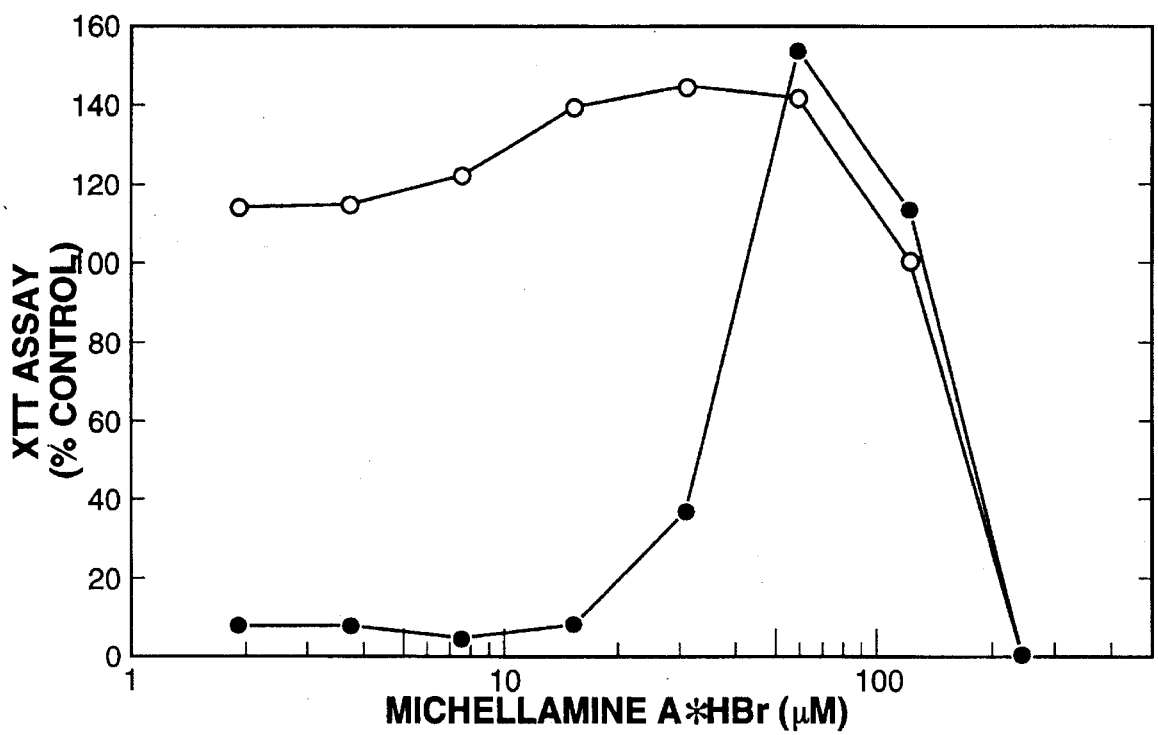
Figure 3D:
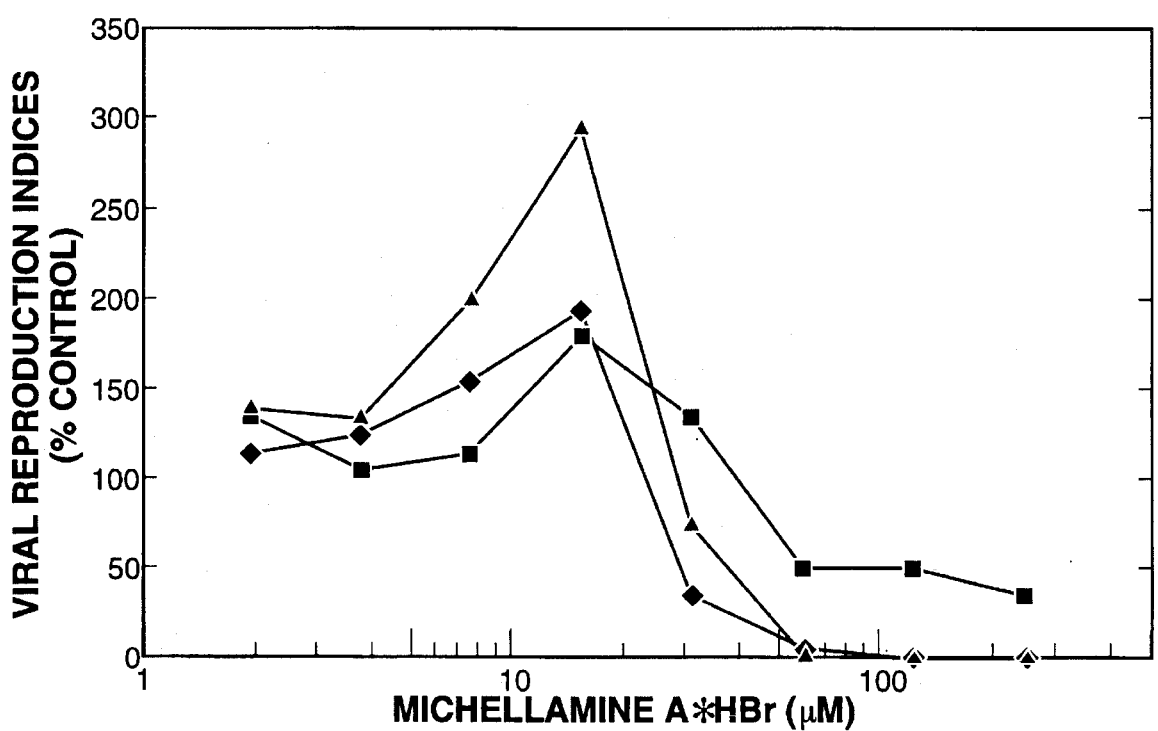
Figure 4A:
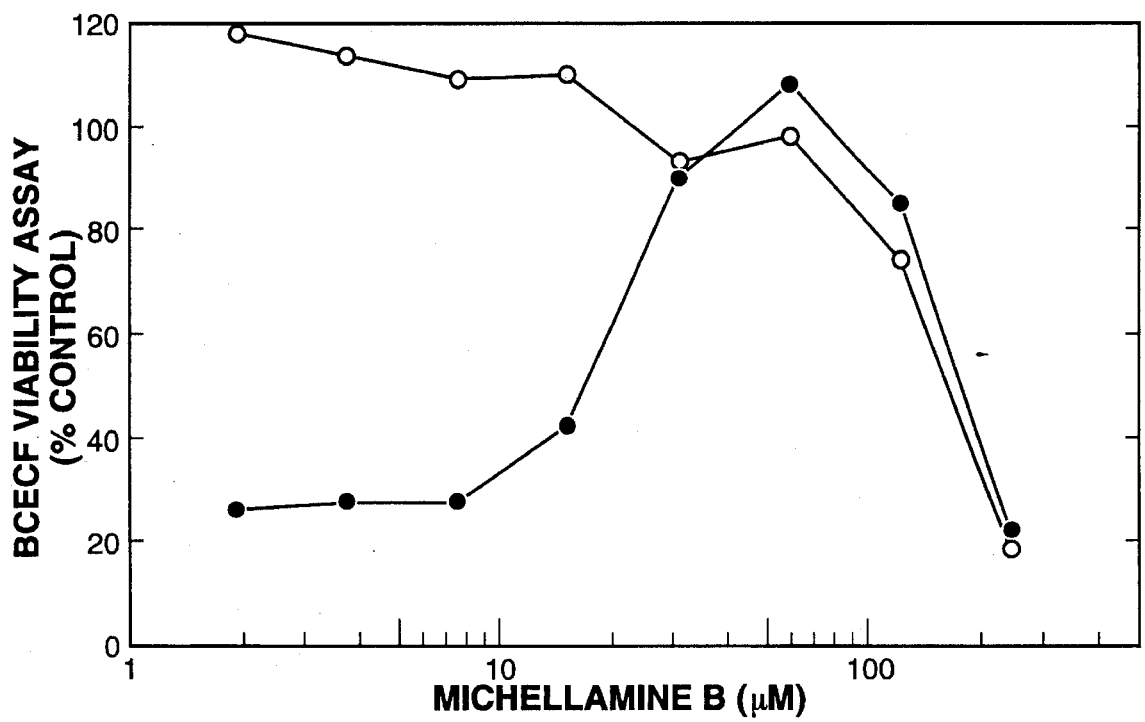
FIGS. 4A–D show the anti HIV-1 activity of michellamine B (free base).
Figure 4B:
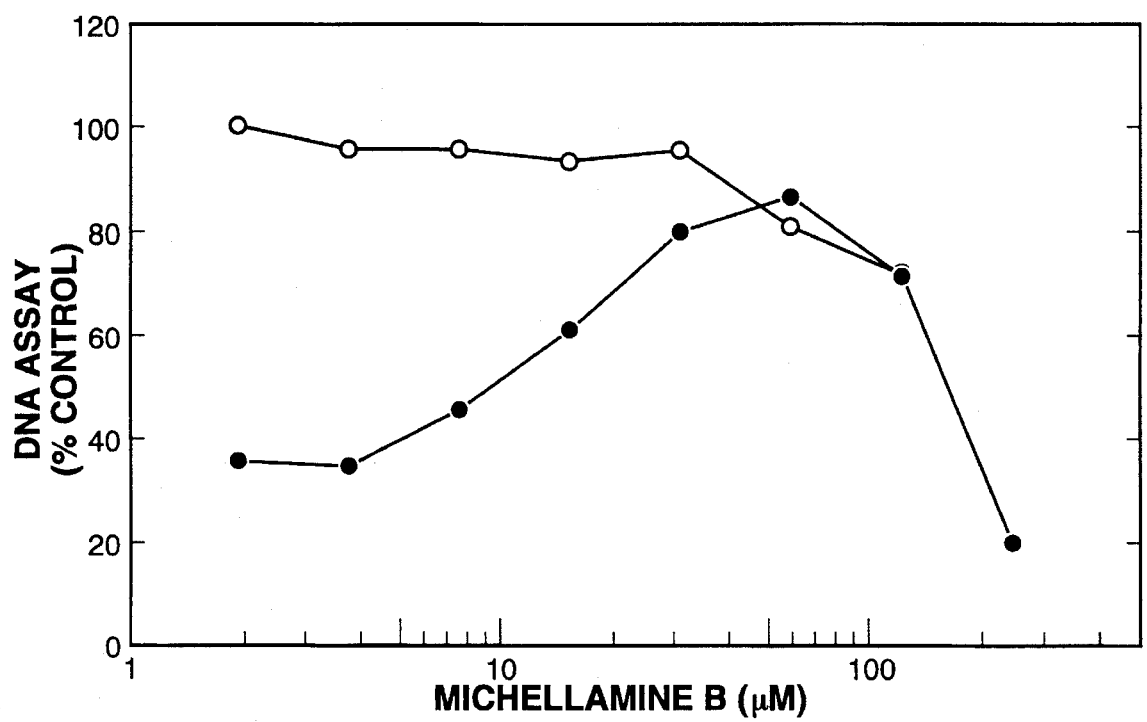
Figure 4C:
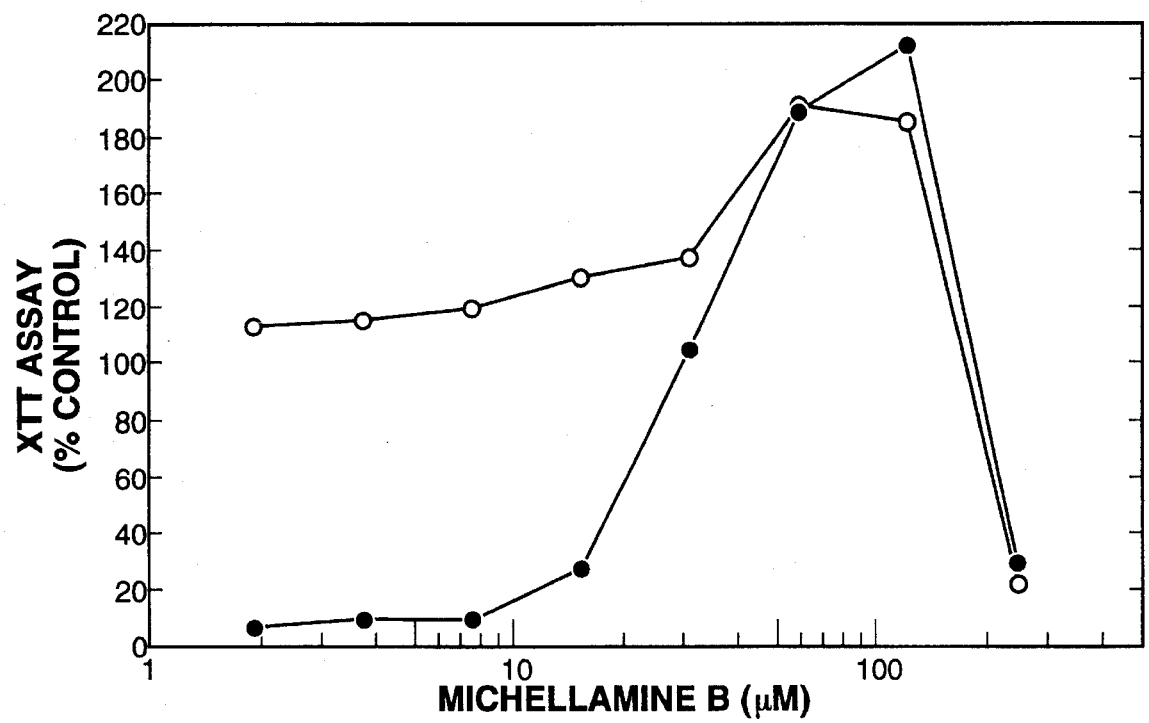
Figure 4D:
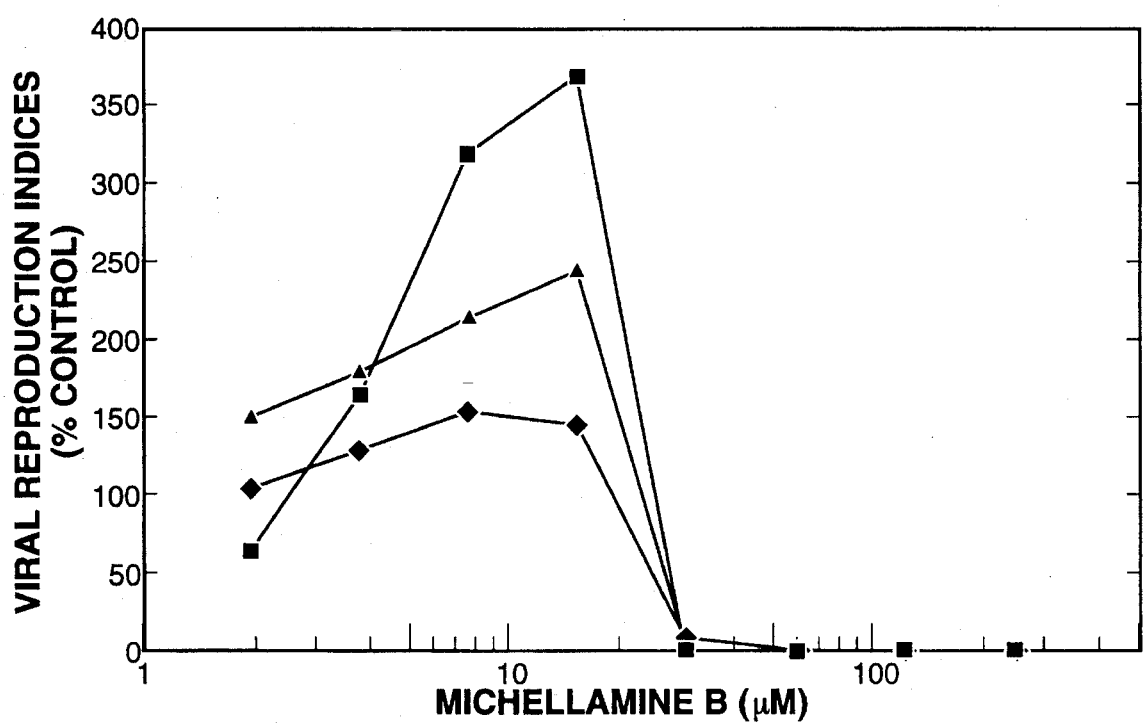
Figure 5A:
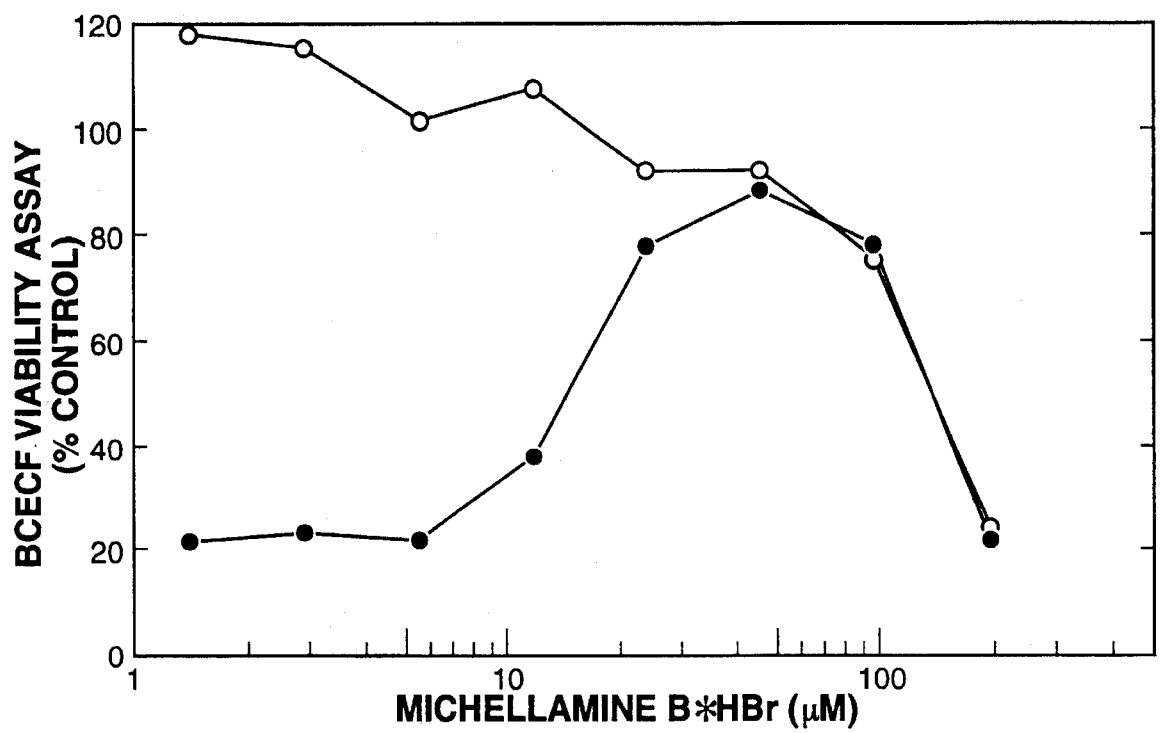
FIGS. 5A–D show the anti-HIV-1 activity of michellamine B (HBr salt).
Figure 5B:
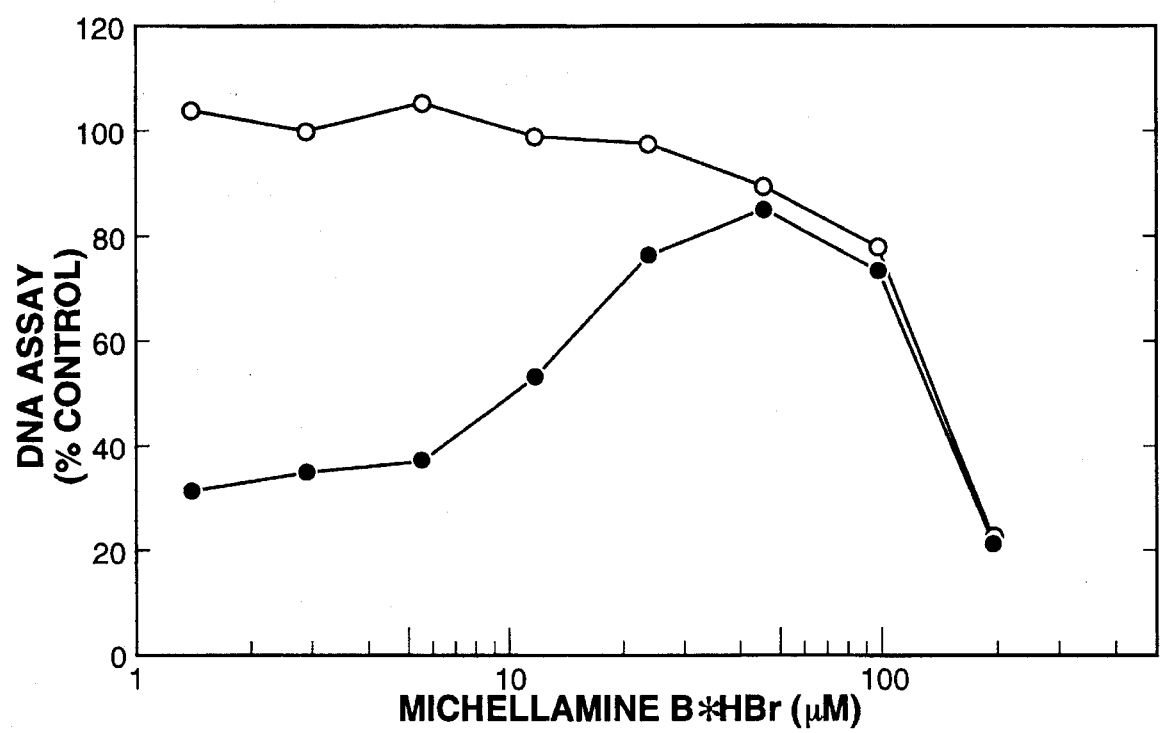
Figure 5C:
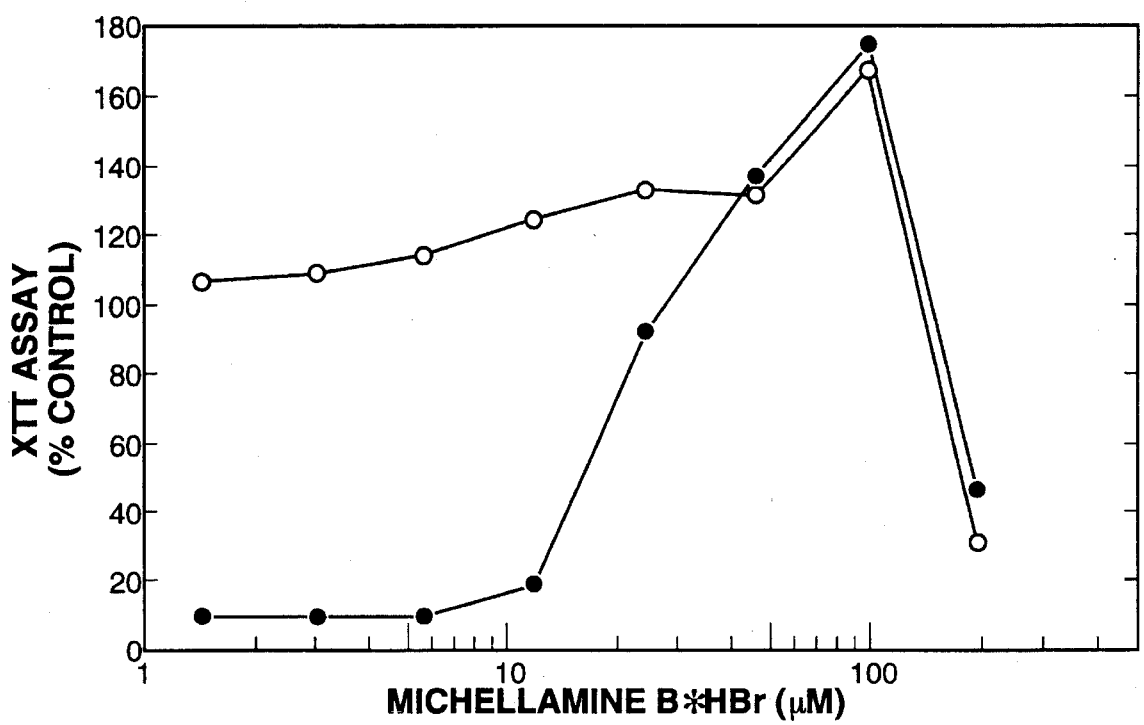
Figure 5D:
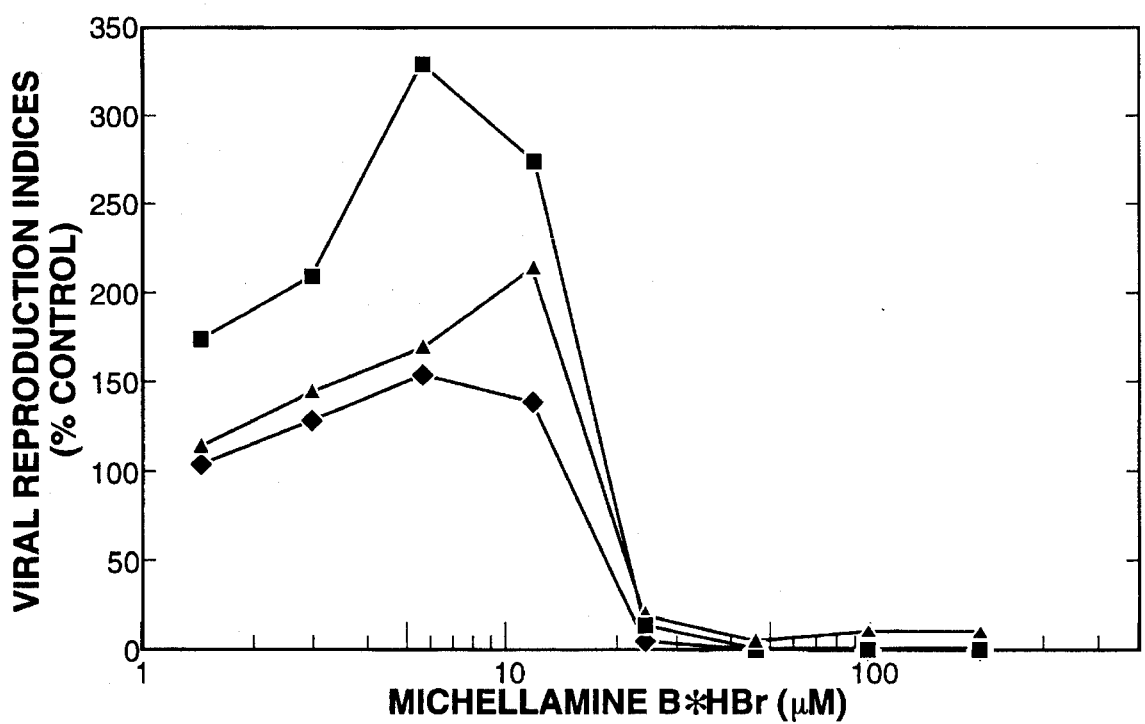

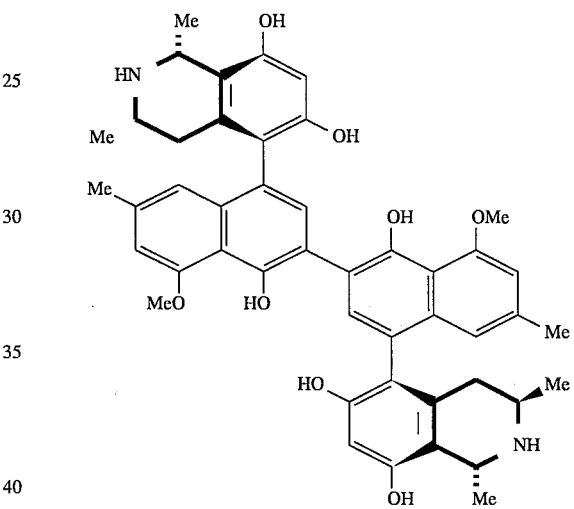

or a pharmacologically acceptable salt thereof. The present invention provides such compounds in substantially pure form. These specific michellamines are referred to herein as michellamines A, B, and C, respectively, as depicted in FIGS. 1A–C. Michellamines are members of the naphthylisoquinoline alkaloid class of compounds. Literature precedents (e.g., Bringmann, The Naphthyl Isoquinoline Alkaloids, in *The Alkaloids*, Vol. 29, Brossi, ed., Academic Press, New York, 1986, pp. 141–184; Bringmann, et al., *Planta Med.*, 58 (Suppl. 1), 703–704 (1992)) from other plant-derived compounds of this general class support that michellamines or michellamine derivatives, having different absolute configurations about one or more of the stereocenters at C-1, C-3, C-1''' or C-3''', might be isolated from natural sources or be synthesized chemically.

Therefore, as one skilled in the art will readily appreciate, the present invention more generally provides a substantially pure michellamine or michellamine derivative having the formula:

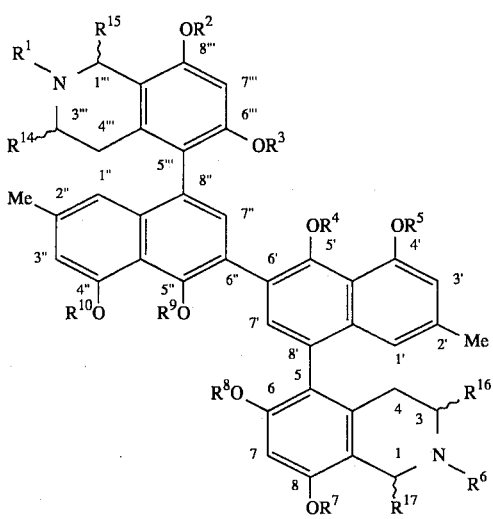

or a pharmacologically acceptable salt thereof, particularly a substantially pure compound having the formula:

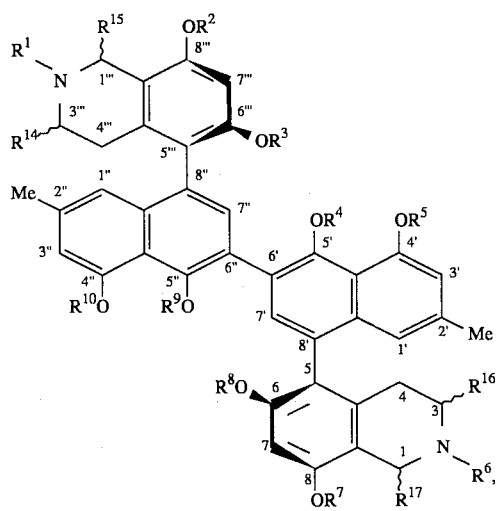

or

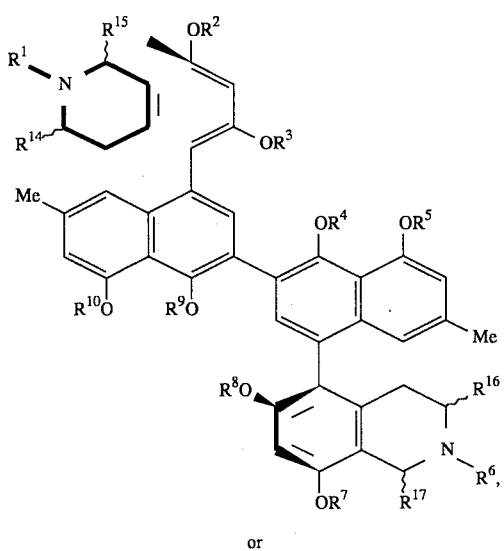

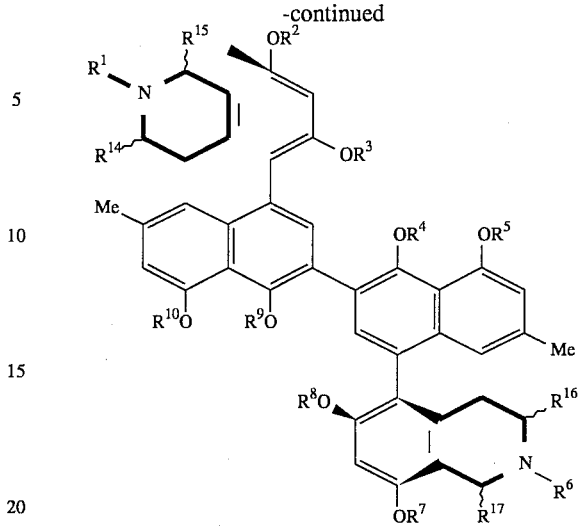

wherein $R^1$ and $R^6$ are the same or different and are each H, $C_1$–$C_6$ alkyl, $R^{11}CO$—, or $R^{11}SO_2$— wherein $R^{11}$ is $C_1$–$C_6$ alkyl or aryl;

$R^2$, $R^3$, $R^4$, $R^7$, $R^8$ and $R^9$ are the same or different and are each H, $C_1$–$C_6$ alkyl, $R^{11}CO$—, $R^{11}SO_2$— wherein $R^{11}$ is defined above;

$R^5$ and $R^{10}$ are the same or different and are each H, $C_1$–$C_6$ alkyl,

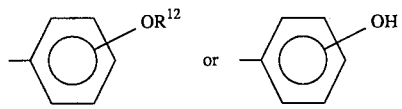

wherein $R^{12}$ is $C_1$–$C_6$ alkyl or $R^{13}CO$— or $R^{13}SO_2$—, wherein $R^{13}$ is $C_1$–$C_6$ alkyl or aryl;

$R^{14}$, $R^{15}$, $R^{16}$ and $R^{17}$ are the same or different and are each ◀CH₃   or   •••CH₃;

and wherein one or more of the ring H positions at 1', 3', 7', 4, 7', 1", 3", 7", 4'''and 7''' can be substituted with a halogen, nitro, amino, hydroxyl, thiol or cyano group, or pharmacologically acceptable salt thereof.

The present inventive method of isolating one of the aforementioned michellamines, particularly michellamine A, B, or C, from *Ancistrocladus sp. novum* (DT 6889) comprises (a) extracting dried plant material with an organic solvent to obtain a crude extract, (b) acid-base partitioning the crude extract to obtain a crude organic base fraction, (c) subjecting the crude organic base fraction to centrifugal partition chromatography, and (d) isolating the michellamines with an amino-bonded phase HPLC column. The present inventive method of interconverting michellamines A or B into a mixture of michellamines A, B, and C comprises (a) dissolving michellamines A or B in an organic solvent and (b) reacting the michellamines A or B with a base. While any suitable organic solvent and base may be used, the organic solvent is preferably an alcohol such as methanol, and the base is preferably sodium hydroxide.

The present inventive composition is an antiviral composition which comprises a pharmaceutically acceptable carrier and an antiviral effective amount of at least one of the aforementioned michellamines, particularly michellamines A, B, or C, derivatives thereof, or pharmacologically acceptable salts thereof. The present inventive composition may include other active or inactive components, in particular, other antiviral agents such as an antiviral effective amount of AZT or other known effective antiviral agent.

The present inventive method of treating a viral infection comprises administering to a patient in need thereof an antiviral effective amount of at least one of the aforementioned michellamines, particularly michellamines A, B, or C, derivatives thereof, or pharmacologically acceptable salts thereof. The treatment method may involve the use of the aforementioned antiviral compositions, and, thus, the treatment method may involve the use of pharmaceutically acceptable carriers and the coadministration of other active or inactive components, in particular, other antiviral agents such as an antiviral effective amount of AZT or other known effective antiviral agent. The particular infecting virus may be any suitable virus, particularly a retrovirus such as human immunodeficiency virus (HIV), including HIV-1 and HIV-2.

Definitions

The pharmacologically acceptable salts may be any such suitable salts. Examples of pharmacologically acceptable salts include HBr, HCl, oxalate, citrate, acetate, tartrate salt, and the like.

By $C_1-C_6$ alkyl is meant straight or branched chain $C_1-C_6$ alkyl groups. Examples include, but are not limited to, methyl, ethyl, n-propyl, iso-propyl, n-butyl, iso-butyl, sec-butyl, tertiary-butyl, n-pentyl, iso-pentyl and n-hexyl.

By aryl is meant an organic radical derived from an aromatic hydrocarbon. An example of an aryl group is phenyl.

By aliphatic is meant organic radical derived from an open hydrocarbon chain. Examples of aliphatic radicals include alkanes, alkenes and alkynes. Specific examples of aliphatic radicals which can be used in the present invention include, but are not limited to, $C_1-C_6$ alkyl radicals, straight or branched.

Of the viral infections that can be treated, examples include, but are not limited to, Type C and Type D retroviruses, HTLV-1, HTLV-2, HIV-1, HIV-2, feline leukemia virus, simian immunodeficiency virus, murine leukemia virus, bovine leukemia virus, equine infections, anemia virus, avian sarcoma viruses, such as rous sarcoma virus and the like, hepatitis type A, B, non A/non B, herpes viruses type 1 and 2, cytomegaloviruses, influenza viruses, arboviruses, varicella viruses, measles, mumps, and rubella viruses.

*Ancistrocladus sp. novum* (DT 6889)

The present inventive compounds are isolated from a newly identified plant species of the genus Ancistrocladus, now tentatively named *Ancistrocladus sp. novum* (DT 6889). A preliminary communication (Manfredi et al., *J. Med. Chem.*, 34, 3402–3405 (1991)) named the source plant of michellamines as *Ancistrocladus abbreviatus*. See also PCT/US92/02805. However, it subsequently has become clear that *A. abbreviatus* is actually devoid of michellamines and, that the true michellamine-containing plant species, while having many similarities to *A. abbreviatus*, is an Ancistrocladus species previously unknown to science.

The Ancistrocladaceae is a small paleotropical family in the order Theales, with about 20 species known from Asia and tropical Africa. So far, ten species have been described from Africa. *Ancistrocladus sp. novum* (DT 6889), presently the only known source of michellamines, differs from all previously described African species of Ancistrocladus in having petals slightly shorter than the sepals; the petals are about twice as long as the sepals in other species. The original specimen of the plant from which antiviral activity first was detected was collected (collection #6889) on Mar. 25, 1987 by Duncan Thomas (DT) in the Korup National Park, west of Mundemba Town in Cameroon's Southwest Province (5°01'N; 8°51'E, 60 m elevation above sea level). Because as yet it has no validly published name, the plant is referred to herein as "species novum" or SP. novum (i.e., new species), followed by the plant collector's name or initials and the collection number that refers to a herbarium specimen. A specimen of the new species (DT 6889) is preserved in the herbarium of the Missouri Botanical Garden, where it is available for viewing by the public.

Although the new species is unique in Africa for the short petals described above, it can also be distinguished by other characteristics. Some of the other species in the genus have a pseudo-petiole, where the leaf blade narrows abruptly towards the base of the leaf, and the basal portion is very narrow. In the new species, the leaf blade narrows gradually to the base. This characteristic distinguishes *Ancistrocladus Sp. novum* from *A. abbreviatus*, *A. barteri*, *A. elalensis*, *A. letestui*, *A. robertsoniorum*, and *A. uncinatus*.

Besides having longer petals, other African species of Ancistrocladus differ from the new species (DT 6889) in the following ways:

| | |
|---|---|
| *A. abbreviatus* (Airy-Shaw): | pseudo-petiole, much shorter inflorescences |
| *A. barteri* (Sc. Elliot): | pseudo-petiole, no intramarginal nerve |
| *A. congensis* (J. Léonard): | pseudo-petiole, smaller leaves |
| *A. ealensis* (J. Léonard): | very slender inflorescences |
| *A. guineenis* (Oliver): | leaf margin involute at the base, blade thinner |
| *A. letestui* (Pellegr.): | small narrow leaves with a pronounced pseudo-petiole |
| *A. likolo* (J. Léonard): | nerves prominent below |
| *A. pachyrrhachis* (Airy-Shaw): | inflorescence very narrow with thick rachis |
| *A. robertsoniorum* (J. Léonard): | slight pseudo-petiole, smaller leaves |
| *A. uncinatus* (Hutch & Dalz): | leaves small, pseudo-petiole |

*Ancistrocladus sp. novum* (DT 6889) is not the only undescribed species in the genus from Cameroon. For example, *Ancistrocladus sp. novum* (D. Thomas 9016, sterile; Cheek and Ndumbe 3915, flowers), found near Douala and Limbe, has large rather thin leaves, short inflorescences, and white flowers with long petals; it does not appear to contain michellamines.

It will be proposed that the new michellamine-bearing species *Ancistrocladus sp. novum* (DT 6889) be formally named *Ancistrocladus korupensis*. However, this name is not considered official until it has been published in a recognized botanical journal; it is anticipated that publication will take place during 1993–94.

No detailed comparisons have been made between the new species and those described from Asia. However, it appears unlikely that a narrowly endemic species from lowland evergreen forest in western Africa would be conspecific with a plant from Asia.

Distribution of *Ancistrocladus sp. novum* (DT 6889)

As far as is known, the new species occurs only in a small area in the Southwest Province of the Republic of Cameroon and possibly in adjacent parts of Cross River State, Nigeria. However, the area is poorly known botanically, and in the future the species may be found elsewhere.

The only known Cameroon collections have been made from a small area of forest west of Mundemba Town, partly inside the Korup National Park. This area has high rainfall (about 5,000 mm per year) most of which occurs in the single, long, wet season from April to November. The soil on which the plants have been found in Cameroon is a leached, nutrient poor, sandy clay. One old (sterile) collection has been made in the Oban area of southeastern Nigeria, about 45 km west of the original Cameroonian collection sites.

The forest in which *Ancistrocladus sp. novum* (DT 6889) occurs is part of an ancient refuge area—that is, an area thought to have been continuously forested during the pleistocene period. This refuge, very rich in rare and endemic species, extends from the Cross River in southeastern Nigeria through Cameroon and to the Mayombe forests of the Congo Republic. The refuge extends up to about 200 km inland; it is still largely covered with species-rich lowland rain forest. The new species could conceivably be found anywhere within this refuge area, but may be unlikely to be found outside it. It is most likely to be discovered in areas close to its present known localities.

Availability of *Ancistrocladus sp. novum* (DT 6889) Leaves

The current known population is small and partly situated in a National Park (5°01'N; 8°47'E–8°52'E), where collecting should not be carried out. The remaining population grows in a small area of forest north of the PAMOL oil palm plantation at Ndian and east of the Korup National Park boundary, which is formed by the Mana (Ndian) river at that point (5°01½'N; 8°52½'E).

The forest outside the park has no known clear ownership at present and is defined as "National Land", belonging to the Cameroon Government. The forest is threatened in the long term both by commercial logging and by conversion to agricultural land. It is anticipated that the areas of unprotected forest in which the vine occurs will be protected by the Cameroon Government through the creation of one or more Forest Reserves.

At present, the known resource appears to be sufficient for initial drug development. The leaves of the plant are richest in michellamine content. A survey is in progress to ascertain the effects of leaf harvesting on the continued viability of the vines. So far, none of the vines from which leaves were harvested has died, but the vine's rate of recovery is not yet known. Other ongoing research is investigating the distribution and size of the wild population of the plant, as well as methods of propagation and cultivation of the plant. This research will show the quantities of michellamine-containing Ancistrocladus leaves which can be expected from the wild population, and how this might be augmented or replaced by cultivated material. This research will critically set the stage for a rapid increase in the quantity of Ancistrocladus leaves available, should demand for the michellamines increase rapidly.

Isolation of the Michellamines from Plant Extracts

A variety of methods can be used to isolate the michellamines. Among these methods are extraction, solvent-solvent partitioning, centrifugal partition chromatography, gel permeation chromatography and HPLC with a variety of bonded phases. The isolation of the compounds can be monitored by UV, TLC, and anti-HIV bioassay.

The procedure described herein is of a scale to accommodate an initial starting amount of approximately ½ kilogram of the air-dried plant material consisting of leaves, stems, and twigs. This plant material is first ground to a coarse powder and extracted with 1:1 MeOH:$CH_2Cl_2$, followed by a second extraction with methanol. These initial crude organic extracts typically amount to a total of approximately 8–10% of the mass of the original dried plant material. This crude extract then is dissolved in 5% aqueous HCl and extracted with $CHCl_3$. The aqueous layer is then made basic with concentrated $NH_4OH$ to a pH of 10–11; it is then extracted with 4:1 $CHCl_3$:MeOH and then with 1:1 MeOH:$CHCl_3$ to give a total of about 0.5–1.0 g of basic extract after removal of the solvent. The extract is then dissolved in the lower phase of a 5:5:3 ($CHCl_3$:MeOH:0.5% aqueous HBr) biphasic solvent system and placed on a Sanki CPC operating in the descending mode. The effluent is monitored at 270 nm. The final peak to elute in descending mode contains the HBr salts of both michellamines A and B plus a trace of C. After removal of the solvent, this mixture typically comprises a total mass of about 200–300 mg. The mixture is further separated with amino-bonded phase HPLC using 43:7 $CHCl_3$:MeOH/0.075% $(NH_4)_2CO_3$ as the solvent. Using this general procedure, the overall yield of michellamines from crude organic extract is about 0.5–2% for michellamine A and 2–10% for michellamine B. Michellamine C is isolated in trace amounts following the same procedure.

EXAMPLES

The following examples further illustrate the present invention but, of course, should not be construed as in any way limiting its scope.

Example 1

This example illustrates the isolation of michellamines from the plant species *Ancistrocladus sp. novum* (DT 6889).

The leaves and stems of dried *Ancistrocladus sp. novum* (DT 6889) (449 g) were ground in a Wiley mill and extracted with 1:1 MeOH—$CH_2Cl_2$ in a Kimax percolator. The ground material was allowed to steep in the solvent overnight. The solvent was removed by filtration and evaporated at reduced pressure to give 36.62 g of crude organic extract.

A portion (2.107 g) of this extract was suspended/dissolved in 330 ml of 5% aqueous HCl and extracted with four 100 ml aliquots of $CHCl_3$. The extracts were combined and the solvent removed at reduced pressure to give 0.657 g of extract. A primary anti-HIV assay was performed according to the procedure set forth in Weislow et al., *J. Natl. Cancer Inst.*, 81, 557–586 (1989), and the material was found to be inactive.

The remaining aqeous layer was treated with concentrated $NH_4OH$ until the pH of the solution was between 10 and 11. The basic aqueous phase was extracted with five 100 ml aliquots of 4:1 $CHCl_3$:MeOH. The extracts were combined and the solvent removed at reduced pressure to give 0.3195 g of extract. An anti-HIV assay was run according to the procedure set forth in Weislow et al., supra, and the material was found to be active.

The remaining aqueous layer was extracted further with three 100 ml aliquots of 1:1 MeOH:$CHCl_3$. The extracts were combined and the solvent removed at reduced pressure to give 0.2534 g of extract, which was again tested according to the same assay (Weislow et al., supra). The material was found to be active.

NMR and TLC analyses of the two active extracts indicated that both samples contained the same compounds. An aliquot of extract from the 4:1 CHCl$_3$:MeOH procedure (264.1 mg) was dissolved in a small amount of the lower phase of a 5:5:3 MeOH:CHCl$_3$:0.5% aqueous HBr biphasic system. This sample was injected into a Sanki centrifugal partition chromatograph (CPC) operating in the descending mode with 12 analytical cartridges (400 rpm, 3.0 ml/min). The effluent was monitored at 270 nm using a Linear UV/Vis 200 monitor. Eight fractions were collected (A-H) while the instrument was operating in the descending mode, and a ninth fraction was collected (I) when the instrument operation was reversed to the ascending mode. Fractions A, C, E, and F were inactive in the anti-HIV assay (Weislow et al., supra). Fractions B (14.4 mg), D (9.0 mg), and I (31.8 mg) showed relatively little activity in the anti-HIV assay. The majority of the anti-HIV activity was found in fractions G (72.7 mg) and H (45.4 mg).

Fraction H (45.4 mg) was dissolved in 500 μl of CHCl$_3$:MeOH (43:7) and injected onto a Waters Delta Prep HPLC using a Rainin Dynamax NH$_2$ column (21.4 mm×250 mm equipped with a guard column). The sample was eluted with CHCl$_3$: MeOH/0.075% (NH$_4$)$_2$CO$_3$ (43:7) at a flow rate of 13 ml/min and monitored at 260 nm. Six fractions were collected and tested for HIV-inhibitory activity. Fractions 1 (retention time =10 min., 1.1 mg), 2 (retention time=19 min., 4.3 mg), 4 (retention time=26 min., 4.6 mg), and 5 (retention time=31.5 min., 1.0 mg) were found to be inactive. Fraction 3 proved to be michellamine A (retention time=22 min., 10 mg), and fraction 6 proved to be michellamine B (retention time=36 min., 14.4 mg). Their chemical and spectral characteristics are set forth below.

Fraction G was treated in a similar manner, except that it was dissolved in 1.5 ml of solvent and placed on the column in three 500 μl injections. From this sample, 5.0 mg of michellamine A and 39.5 mg of michellamine B were obtained. 3.0 mg of an inactive, unidentified compound were also collected.

The sample obtained from the MeOH:CHCl$_3$ (1:1) extract described above (251 mg) was placed on the Sanki CPC under the same conditions as the 4:1 extract. In this case, seven fractions were collected while the instrument was operated in the descending mode (A-G) and one fraction collected during the ascending mode (H).

Fractions A, B, C, D, and H were inactive in the anti-HIV assay, while E, F, and G were all active. Preparative HPLC of Fraction E (72.4 mg), under the identical conditions as above, afforded 0.8 mg of michellamine A, 44.5 mg of michellamine B, and 6.3 mg of an inactive tetrahydroisoquinoline compound. Fraction F (18.8 mg) afforded 2.8 mg of michellamine A and 8.1 mg of michellamine B along with two minor inactive compounds (< 2 mg). Fraction G (18.2 mg) afforded 10.1 mg of michellamine A and 2.1 mg of an unknown inactive substance. A third, minor compound, michellamine C, was isolated on one occasion as a shoulder on the michellamine B chromatographic peak. It has not been encountered in subsequent, more rapidly processed material.

The overall yield of the active fractions from starting crude extract was 1.4% michellamine A and 5.0% michellamine B.

Example 2

This example sets forth information on the chemical structures of the michellamines isolated in accordance with Example 1.

An in vitro anti-HIV screening assay, according to the procedure set forth in Weislow et al., supra, initially disclosed AIDS-antiviral activity in the CH$_3$OH—CH$_2$Cl$_2$ (1:1) extracts of *Ancistrocladus sp. novum* (DT 6889). Preliminary fractionation established that the active constituents were basic alkaloids. The crude alkaloid fraction, obtained by acid-base partitioning, was subjected to centrifugal partition chromatography (CHCl$_3$ —CH$_3$OH—0.5% HBr/H$_2$O, 5:5:3), and elution with the lower phase gave four fractions. Fraction 4 yielded two active compounds, related as atropisomers to which were given the names michellamines A and B (FIGS. 1A–B), upon HPLC on an amino-bonded phase semi-preparative column [CHCl$_3$–0.075% (NH$_4$)$_2$CO$_3$/CH$_3$OH, 43.7].

Mass spectral analyses, via plasma desorption mass spectrometry ($^{252}$Cf PDMS), demonstrated that the two compounds had identical molecular weights (m/z 756). The molecular formula was established as C$_{46}$H$_{48}$N$_2$O$_8$ by accurate-mass, fast atom bombardment mass spectrometry.

The family Ancistrocladaceae is well known as a source of naphthalene-tetrahydroisoquinoline alkaloids (Bringmann, Supra; Ruangrungsi et al., *J. Nat. Prod.*, 48., 529–534 (1989), and references cited therein). The mass spectral data and the complex NMR spectra of the isolated compounds suggested that these antiviral compounds were dimeric relatives of the known Ancistrocladaceae alkaloids.

The NMR data for michellamine A are provided in Table 1.

TABLE 1

NMR DATA FOR MICHELLAMINE A

| Carbon # | δ (# attached H) | $^1$H δ (Multiplicity) J (Hz) |
|---|---|---|
| 1/1''' | 49.5 (1) | 4.64 q 6.5 |
| 3/3''' | 45.2 (1) | 3.54 ddq 11.8, 4.3, 6.5 |
| 4/4''' | 33.1 (2) | (e) 2.69 dd 18.6, 4.3; |
|  |  | (a) 2.05 dd 18.6, 11.8 |
| 4a/4a''' | 133.1 (0) |  |
| 5/5''' | 120.3 (0) |  |
| 6/6''' | 156.9 (0) |  |
| 7/7''' | 102.0 (1) | 6.40 s |
| 8/8''' | 155.4 (0) |  |
| 8a/8a''' | 113.1 (0) |  |
| 1'/1'' | 119.1 (1) | 6.75 s |
| 2'/2'' | 137.6 (0) |  |
| 3'/3'' | 108.0 (0) | 6.84 s |
| 4'/4'' | 158.1 (0) |  |
| 4a'/4a'' | 115.2 (0) |  |
| 5'/5'' | 152.2 (0) |  |
| 6'/6'' | 119.0 (0) |  |
| 7'/7'' | 134.8 (1) | 7.30 s |
| 8'/8'' | 124.1 (0) |  |
| 8a'/8a'' | 136.6 (0) |  |
| OMe/OMe | 57.1 (3) | 4.10 s |
| Me-3/Me-3''' | 19.4 (3) | 1.16 d 6.5 |
| Me-1/Me-1''' | 18.4 (3) | 1.57 d 6.5 |
| Me-2'/Me-2'' | 22.1 (3) | 2.33 s |

$^{13}$C (125 MHz) and $^1$H (500 MHz) NMR spectra of the HBr salt were recorded in d$_4$-methanol. # attached H determined from DEPT experiments. The designations "a" and "e" refer to axial and equatorial, respectively.

Other spectral data and other characteristics for michellamine A are as follows: MP=220° C. (dec); [α]$_D$=−10.5°, [α]$_{365}$=+65. 7° (C=0.38, MeOH); FAB-MS: m/z 757.342 (MH+, calc'd for C$_{46}$H$_{49}$N$_2$O$_8$ 757.3487); λ$_{max}$ (MeOH) 230 nm (log ε=4.4), 262(4.1), 287(3.8), 312(3.8) 331(3.8), 344(3.8); ν$_{max}$ (neat) 3380, 1617, 1584 cm$^{-1}$.

The NMR data for michellamine B are provided in Table 2.

TABLE 2

NMR DATA FOR MICHELLAMINE B

| Carbon # | δ (# attached R) | $^1$H δ (Multiplicity) J (Hz) |
|---|---|---|
| 1/1''' | 49.6, 49.3 (1) | 4.44, 4.26 q 6.5 |
| 3/3''' | 45.3, 45.2 (1) | 3.27, 3.21 ddq 11.4, 4.5, 6.5 |
| 4/4''' | 33.9, 33.1 (2) | (eR) 2.49 dd 17.5, 4.5; (aR) 1.86 dd 17.5, 11.0; (aS) 2.22 dd 17.5, 11.0; (eS) 2.08 dd 17.5, 4.5 |
| 4a/4a''' | 133.1, 133.0 (0) | |
| 5/5''' | 120.0, 120.2 (0) | |
| 6/6''' | 156.90, 156.88 (0) | |
| 7/7''' | 102.0, 102.1 (1) | 6.34 s |
| 8/8''' | 155.54, 155.51 (0) | |
| 8a/8a''' | 113.0, 113.2 (0) | |
| 1'/1'' | 119.2, 119.2 (1) | 6.77, 6.86 s |
| 2'/2'' | 137.60, 137.56 (0) | |
| 3'/3'' | 108.12, 108.11 (1) | 6.84, 6.82 s |
| 4'/4'' | 158.0, 158.1 (0) | |
| 4a'/4a'' | 115.22, 115.17 (0) | |
| 5'/5'' | 152.2, 153.3 (0) | |
| 6'/6'' | 119.0, 119.1 (0) | |
| 7'/7'' | 136.7, 136.5 (1) | 7.28, 7.24 s |
| 8'/8'' | 124.12, 124.10 (0) | |
| 8a'/8a'' | 135.2, 134.7 (0) | |
| OMe/OMe | 57.04, 57.05 (3) | 4.08, 4.09 s |
| Me-3/Me-3''' | 19.3, 19.3 (3) | 1.05, 1.01 d 6.5 |
| Me-1/Me-1''' | 18.42, 18.40 (3) | 1.52, 1.48 d 6.5 |
| Me-2'/Me-2'' | 22.1, 22.2 (3) | 2.36, 2.31 s |

$^{13}$C (125 MHz) and $^1$H (500 MHz) NMR spectra were recorded in d$_4$-methanol. $^{13}$C chemical shifts are reported for the HBr salt. $^1$H chemical shifts are reported for the free base. The designations (eS, aS) and (aR, eR) refer to the methylene signals on the isoquinoline systems with the 'S' and 'R' stereochemistry at the 5–8' and 5'''–8''' ring junctures; "a" and "e" refer to axial and equatorial, respectively. # attached H were determined from DEPT experiments.

Other spectral data and other characteristics for michellamine B are as follows: MP=230° C. (dec); $[\alpha]_D$=−14.8°, $[\alpha]_{365}$=−23.4° (C=0.74, MeOH); FAB-MS; m/z 757.350 (MH+, calc'd for C$_{46}$H$_{49}$N$_2$O$_8$ 757. 3487); UV and IR were identical to those reported for michellamine A.

The presence of only 23 resonances in the $^{13}$C-NMR spectrum of michellamine A indicated that the two naphthalene-isoquinoline components were equivalent. The structure and relative stereochemistry of the tetrahydroisoquinoline subunit could be discerned readily from $^1$H—$^1$H coupling constant analysis and difference nOe experiments. The H-3/H-3''' protons served as linchpins in the analysis (the ring-numbering scheme follows the same scheme as in the Bringmann reference cited above). A pseudoaxial position on the ring was evident from its couplings to the H-4/H-4''' protons (11.8, 4.3 Hz); a moderate to strong nOe response to the methyl group attached to C-1/C-1''' established the 1,3 diaxial relationship between the two and therefore the trans relationship between the methyl groups attached to C-1/C-1''' and C-3/C-3'''. The composition of one ring in the naphthalene system was established through HMQC, HMBC, and difference nOe experiments as a pair of meta-disposed protons, with an intervening methyl group and a flanking methoxyl. The remaining ring had a single proton, one hydroxyl group and linkages to two other aryl systems. HMBC and HMQC data suggested a 1,3 relationship of the proton and hydroxyl substituents. The complete substitution of that ring and the relative stereochemistry and conformation of the naphthalene/tetrahydroisoquinoline connection were secured from difference nOe data. Each of the benzylic methylene protons (C-4/C-4''') of the tetrahydroisoquinoline system exhibited an nOe relationship to different naphthalene protons, H-4e/H-4e''' to H-7'/H-7'' and H-4a/H-4a''' to H-1'/H-1''. Thus, the tetrahydroisoquinoline was linked to the naphthalene by a bond from C-5/C-5''' to C-8'/C-8''. The naphthalenes, therefore, had to be connected at C-6'/C-6''.

In contrast, the $^{13}$C-NMR spectrum of michellamine B was comprised of 46 signals. A similar series of NMR experiments provided the same gross structure found for michellamine A. The differences between the two compounds lay in the relative configuration of the ring connections. In michellamine B the C-4 methylene signals appeared as four discreet resonances, and each produced an nOe enhancement of an aromatic proton signal upon irradiation. In one set, the relationships were the same as those for michellamine A: H-4e and H-7', H-4a and H-1'. The relationships were reversed in the other half of the molecule: H-4e''' and H-1', H-4a''' and H-7''. As before, the assignments of the protons in the tetrahydroisoquinoline system were established clearly from coupling constants and the nOe data.

A trace amount of a third atropisomer, to which has been given the trivial name michellamine C (FIG. 1C), also was encountered. The NMR data for michellamine C are provided in Table 3.

TABLE 3

NMR DATA FOR MICHELLAMINE C

| Carbon # | δ (# attached H) | $^1$H δ (Multiplicity) J (Hz) |
|---|---|---|
| 1/1''' | 49.1 (1) | 4.73 q 7.0 |
| 3/3''' | 45.0 (1) | 3.65 ddq 11.5, 5.0, 6.5 |
| 4/4''' | 34.3 (2) | (a) 2.62 dd 17.5, 11.5; (e) 2.35 dd 17.5, 5.0 |
| 4a/4a''' | 133.5 (0) | |
| 5/5''' | 120.3 (0) | |
| 6/6''' | 156.6 (0) | |
| 7/7''' | 102.0 (1) | 6.43 s |
| 8/8''' | 155.6 (0) | |
| 8a/8a''' | 113.9 (0) | |
| 1'/1'' | 119.3 (1) | 6.84 s |
| 2'/2'' | 137.4 (0) | |
| 3'/3'' | 108.0 (1) | 6.85 s |
| 4'/4'' | 158.0 (0) | |
| 4a'/4a'' | 115.2 (0) | |
| 5'/5'' | 152.2 (0) | |
| 6'/6'' | 119.0 (0) | |
| 7'/7'' | 135.3 (1) | 7.28 s |
| 8'/8'' | 124.3 (0) | |
| 8a'/8a'' | 136.4 (0) | |
| OMe/OMe | 57.0 (3) | 4.09 s |
| Me-3/Me-3''' | 19.6 (3) | 1.30 d 6.5 |
| Me-1/Me-1''' | 18.6 (3) | 1.68 d 7.0 |
| Me-2'/Me-2'' | 22.2 (3) | 2.36 s |

$^{13}$C (125 MHz) and $^1$H (500 MHz) NMR spectra of the free base were recorded in d$_4$-methanol. The designations "a" and "e" refer to axial and equatorial, respectively. # attached H were determined from DEPT experiments.

Michellamine C appears to have the opposite configuration from michellamine A about the C-5/C-8' and C-5'''/C-8'' bonds. Variable temperature NMR experiments failed to show evidence of spontaneous interconversion.

Molecular modeling calculations determined the barrier to rotation about the C-5/C-8' (and C-5'''/C-8'') bond in the michellamines to be 81 KJ/mole; in contrast, the calculated barrier for rotation about the C-6'/C-6'' bond (51 KJ/mole) was within the range for available thermal energy to enable rotation past the barrier (Still et al., *Macromodel*, V 2.5, Dept. of Chemistry, Columbia University, N.Y.).

The michellamines are unique molecules in several regards. They are the first dimeric alkaloids of this class to be discovered, and they possess an unusual C-5/C-8' (and C-5'''/C-8'') linkage between the two ring systems. Further, they are the most polar compounds in the class, containing more free phenols per monomeric unit than any of the known compounds. The originally-depicted (Manfredi et al., supra) absolute stereochemistry of the michellamines was arbitrarily assigned based upon literature precedents (e.g., Bringmann, supra). Until recently, none of the known "monomeric" alkaloids contained such a C-5/C-8' linkage; however, the structure of a monomeric naphthylisoquinoline alkaloid, ancistrobrevine B, which contains the C-5/C-8' linkage, was reported (Bringmann et al., *Phytochemistry*, 31, 4011–4014 (1992)).

For definitive determination of the absolute configurations of the michellamines, an efficient ruthenium-mediated oxidative degradation procedure, recently introduced in the field of "monomeric" naphthylisoquinoline alkaloids (Bringmann et al., supra), was extended to the dimeric compounds. This analysis is based upon the configurations of resulting amino acids, 3-aminobutyric acid derived from C-3, and alanine derived from C-1. A specific example follows.

Michellamine B (9.3 mg, 12.4 µmol) was added to 4 mL of a mixture of MeCN/CCl$_4$/aqueous phosphate buffer (pH= 6)(1:1:2) under stirring at room temperature, followed by RuCl$_3$·3H$_2$O (0.1 mg) and NaIO$_4$ (99 mg). After 2.5 h, the aqueous phase was separated and lyophilized. The residue was extracted with dry MeOH. The resulting solution, which contained the product amino acids, was saturated with gaseous HCl at 0° C. and stirred at room temperature for 3 h to yield the corresponding methyl esters. After evaporation of the solvent, the residue was suspended in dry CH$_2$Cl$_2$ (1 mL). Subsequently, NEt$_3$ (0.2 mL) and (R)-α-methoxy-α-trifluoromethylphenylacetic acid chloride (MTPA-C$_1$) (46 µmol, prepared from the corresponding (S)-acid) were added to give the Mosher derivatives of the esters after stirring at room temperature for 1 h. These were analyzed by FID-GC and found to be derived from D-alanine ($t_R$=15.6 min) and (R)-β-aminobutyric acid ($t_R$= 21.2 min). These assignments were confirmed by co-injection with the corresponding racemic as well as enantiomerically pure amino acid standards. The FID-GC data were obtained on an OV1-column (0.33 mm×30 m); temperature program: from 140° C. (1 min) to 155° C. (1 min) at 1° C./min, from 155° C. (1 min) to 160° C. (1 min) at 0.5° C./min.

From the exclusive formation of both amino acids in their R-configurations, michellamine B was unambiguously established to have R-configurations at C-1 and C-3 of both "molecular halves". Given the relative configuration at the two stereogenic biaryl axes (at C-5/C-8' and C-5'''/C-8'') of the two molecular halves) vs. the stereocenters, as deduced from the NOE experiments (see above), the complete absolute stereostructure of michellamine B therefore was established as 1R, 3R, 5R (or M), 1'''R, 3'''R, 5'''S (or P), depicted in FIG. 1B. Michellamine A likewise was subjected to the same degradation analysis, and its absolute stereostructure established similarly as 1R, 3R, 5S (or P), 1'R, 3'''R, 5'''S (or P), as depicted in FIG. 1A. Since the NMR data had indicated opposite configurations at the C-5/C-8' (and C-5'''/C-8'') linkages in michellamine A versus C, the absolute stereostructure in michellamine C was deduced to be 1R, 3R, 5R (or M), 1'''R, 3'''R, 5'''R (or M), as depicted in FIG. 1C. Thus, differing from many other Ancistrocladaceae-alkaloids (Bringmann, supra), the michellamines have an oxygen function at C-6, but R-, not S-configuration at C-3.

The complete structural assignments, as deduced from the elucidation of the relative configurations of axial vs. central chirality within the "halves" combined with the knowledge of the absolute configuration at the stereocenters, as evident from the oxidative degradation reaction, was confirmed further by the circular dichroism (CD) of michellamines A, B, and C. As for other naphthylisoquinoline alkaloids, the CD-behavior is greatly dominated by the element of axial chirality.

Thus, michellamine A, in which both axes have P-configurations, exhibited very strong Cotton effects [CD: 25° C.; $\Delta\epsilon_{200}$–17, $\Delta\epsilon_{200.5}$–118, $\Delta\epsilon_{202}$ –40, $\Delta\epsilon_{210.5}$–521, $\Delta\epsilon_{233.5}$+210, $\Delta\epsilon_{242.5}$+84, $\Delta\epsilon_{255.5}$+129, $\Delta\epsilon_{281.5}$–7, $\Delta\epsilon_{296}$+24, $\Delta\epsilon_{318}$–48, $\Delta\epsilon_{326}$–44, $\Delta\epsilon_{333}$–52, $\Delta\epsilon_{350}$–14 (EtOH; c 0.02)], due to the identical stereochemistry at the two axes. The CD-curve was essentially opposite to that of ancistrobrevine B [CD: 25° C.; $\Delta\epsilon_{200}$–64, $\Delta\epsilon_{209}$+101, $\Delta\epsilon_{215}$+88, $\Delta\epsilon_{226}$+191, $\Delta\epsilon_{239}$–134 (EtOH; c 0.088)] which is structurally closely related to the molecular half of michellamine A, but has the opposite (M) configuration at the axis. This underscores further the correct assignment of the absolute configuration of both biaryl axes of michellamine A as P.

In michellamine B, the CD-curve had a distinctly less pronounced character [CD:25° C.; $\Delta\epsilon_{200}$+15, $\Delta\epsilon_{201}$–34, $\Delta\epsilon_{201.5}$ +24, $\Delta\epsilon_{202.5}$–68, $\Delta\epsilon_{203.5}$–31, $\Delta\epsilon_{205}$–92, $\Delta\epsilon_{205.5}$–40, $\Delta\epsilon_{208}$ –116, $\Delta\epsilon_{210}$–116, $\Delta\epsilon_{210.5}$–130, $\Delta\epsilon_{218.5}$–158, $\Delta\epsilon_{219.5}$+1, $\Delta\epsilon_{231.5}$+0, $\Delta\epsilon_{242}$–75, $\Delta\epsilon_{276}$+0, $\Delta\epsilon_{299}$+76, $\Delta\epsilon_{338}$ –31, $\Delta\epsilon_{350}$–22 (EtOH; c 0.021)]. This logically was due to the opposite contributions of the two axes to the molar ellipticities, the CD-graph mainly arising from the contributions of the stereocenters (and possible chiral interactions between the molecular halves).

In further confirmation of the absolute configuration of michellamine C, the 200–240 nm region of the CD-curve was found to be nearly opposite to that of michellamine A [CD: 25° C.; $\Delta\epsilon_{200}$+57, $\Delta\epsilon_{200.5}$+116, $\Delta\epsilon_{201}$+71, $\Delta\epsilon_{201.5}$+115, $\Delta\epsilon_{202}$+85, $\Delta\epsilon_{207.5}$+373, $\Delta\epsilon_{238}$–238, $\Delta\epsilon_{271.5}$–4, $\Delta\epsilon_{272}$+6, $\Delta\epsilon_{295.5}$+156, $\Delta\epsilon_{311}$+156, $\Delta\epsilon_{345}$–1, $\Delta\epsilon_{350}$–18 (EtOH; c 0.011)].

Example 3

This example illustrates a procedure for the preparation of HBr salts of the michellamines as obtained in Example 1.

A solution of michellamine B in MeOH was treated dropwise with 9M HBr (2.2 mole equivalents). After addition was complete, the solvents were evaporated, providing the HBr salt. Other salts of the michellamines have been prepared in a similar manner.

Example 4

This example illustrates a procedure for the interconversion of the michellamines as obtained in Example 1.

To a solution of michellamine A (1 mg in 1 ml MeOH-d$_4$) was added 0.5 ml of 0.5M NaOD/D$_2$O. $^1$H-NMR analysis indicated a slow conversion of michellamine A to a mixture of michellamines A, B, and C (~3:3:1) over a period of 7 days. Likewise, michellamine B was converted to the same mixture under identical conditions. HPLC analyses confirmed these results.

Example 5

This example illustrates a procedure for the preparation of derivatives of the michellamines as obtained in Example 1.

Using standard organic chemical methodology, a number of structural modifications of the michellamines can be made for purposes of preparing derivatives of the michellamines which express antiviral activity.

Depending on the stoichiometric amount of the particular reactant, the michellamines can be substituted at one, some, or all of the respective positions. For example, when one of the michellamines A, B, or C is reacted with a certain amount of CH₃COCl, acetate can be substituted at one, some, or all of $R^2$, $R^3$, $R^4$, $R^7$, $R^8$, and $R^9$. Likewise, when one of the michellamines A, B, or C is reacted with a certain amount of benzene sulfonyl chloride, one or both of $R^1$ and $R^6$ can form benzene sulfonamide derivatives.

Examples of these include, but are not limited to:

1. Preparation of ester, sulfonate ester, and ether derivatives at one or more of the six phenolic hydroxyl positions in the michellamines (C-5≡, C-6, C-8).

For preparation of esters or sulfonate ester, michellamine A or B can be reacted with an acid halide (RCOX or RSO₂X, where X=Cl, Br, or I and R is an $C_1$–$C_6$ aliphatic or an aromatic radical) in anhydrous pyridine or triethylamine.

Alternatively, michellamine A or B can be reacted with an acid (RCO2H or RSO3H wherein R is an aliphatic or aromatic radical) and dicyclohexylcarbodiimide in triethylamine to prepare the ester or sulfonate ester.

For preparation of ethers, michellamine A or B can be reacted with an alkyl halide (RX, where X=Cl, Br, or I and R is an $C_1$–$C_6$ aliphatic or aromatic radical) in anhydrous acetone with anhydrous potassium carbonate. For example:

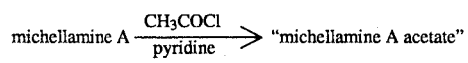

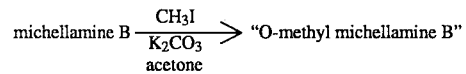

2. Removal of the ether methyl group at C-4' to provide a phenolic hydroxyl functionality and/or conversion of that moiety to an ester, sulfonate, or other ether.

For cleavage of the ether methyl and conversion to phenolic hydroxyl, michellamine A or B is reacted with BBr₃ or BX₃·(CH₃)₂S in CH₂Cl₂ (where X=F, Cl or Br). The resulting phenol can be converted to esters, sulfonate esters or ethers as described above (in 1). For example:

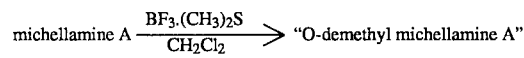

3. Preparation of amide or sulfonamide derivatives at one or both amine sites in the michellamines.

For preparation of amide or sulfonamide derivatives, the same procedures described above (in 1) apply. In either case (1 or 3), an appropriate functional group protection strategy (blocking/deblocking of selected groups) is applied. For example:

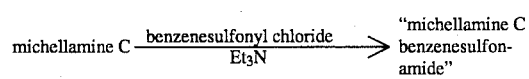

4. Conversion of the secondary amine functionality to a tertiary amine or tetraalkyl quaternary ammonium salt.

For preparation of tertiary amines or tetraalkyl ammonium salts, michellamine A or B is reacted with one or two equivalents of alkyl halide (RX, where X=Cl, Br or I and R is an $C_1$–$C_6$ aliphatic radical) in anhydrous aprotic solvent.

Alternatively, michellamine A or B is reacted with an aldehyde and the resulting product reduced with NaBH₄. For example:

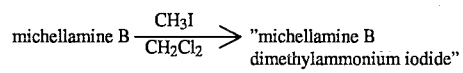

5. Substitution of one or more of the hydrogen substituents on the aryl systems (C-7/C-7''', C-1'/C-1'', C-3'/C-3'', C-7'/C-7'') by halogen, nitro, amino, hydroxyl, thiol, or cyano groups.

For preparation of bromine substituted derivatives, michellamine A or B is reacted with Br₂ in H₂O. For preparation of other substituted derivatives, michellamine A or B is treated with HNO₃/HOAc to provide nitro-substituted (—NO₂) derivatives. In turn, the nitro derivative can be reduced to the amino derivative. The amino-derivative is the point of origin of the chloro, iodo, cyano, thiol, and hydroxyl substitution via well known and practiced diazonium substitution reactions. For example:

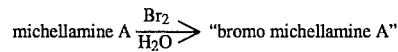

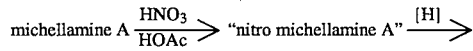

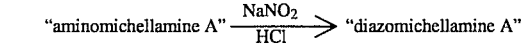

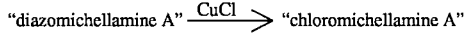

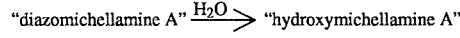

Example 6

This example illustrates the antiviral activity of the compounds of the present invention.

A battery of interrelated assays on individual wells from 96-well microtiter plates was performed to show antiviral activity. Measurements of cellular viability, in the presence and absence of the compounds in uninfected and virus-infected cells, by an adaptation of the procedure set forth in Weislow et al., *J. Natl. Cancer Inst.*, 81, 577–586 (1989), as well as by an adaptation of a method using the fluorescent probe 2'-7'-biscar-boxyethyl-5(6)-carboxyfluorescein acetoxymethyl ester (BCECF) as set forth in Rink et al., *J. Cell Biol.*, 95, 189–196 (1982), were performed as described herein below. BCECF is a nonfluorescent molecule which readily enters viable cells where it is hydrolyzed by cellular esterases to a fluorescent molecule. Total cellular DNA content was measured with the dye, 2-diamidino-phenylindole (DAPI), which fluoresces when intercalated at A-T specific sites in chromatin, according to the procedure set forth in McCaffrey et al., *In Vitro Cell. Develop. Biol.*, 24, 247–252 (1988). These dyes are used in combination with Particle Concentration Fluorescent Immunoassay technology (PCFIA), specifically the Screen Machine™ available from Baxter Healthcare Corporation (Mundelein, Ill.). The Screen Machine is a semiautomated fluorescent plate reader capable of adding reagents and/or wash buffers to filter-bottomed, 96-well plates with the subsequent evacuation of fluid and concentration of fluorescently-stained cells on the cellulose acetate filter. Fluorescence is detected via epifluorescence.

Also concurrent with the above, confirmatory assays of p24 antigen production,-reverse transcriptase activity, and synthesis of infectious virions were performed. These and other details of the procedures and results are described in further detail as follows.

Cells and virus

The human lymphocytic target cell lines, CEM-SS and MT-2, used in the antiviral assays were maintained in RPMI 1640 medium (Gibco, Grand Island, N.Y.) without phenol red and supplemented with 5% fetal bovine serum (FBS) (Gibco), 2 mM L-glutamine, and 50 µg/ml gentamicin (Gibco) (complete medium). Exponentially-growing CEM-SS or MT-2 cells were pelleted and resuspended at a concentration of $2.0 \times 10^5$ cells/ml in complete medium. For the HIV-1 studies, the Haitian variant of HIV, HTLV-III$_{RF}$ was used. For the HIV-2 studies, the NIH-DZ strain or the CBL20 strain was used. Frozen virus stock solutions were thawed immediately before use and resuspended in complete medium to yield $1.2 \times 10^5$ SFU/ml.

Reagents

The tetrazolium reagent, XTT, was obtained from the Drug Synthesis and Chemistry Branch, Developmental Therapeutics Program, Division of Cancer Treatment, National Cancer Institute. Biscarboxyethyl-5(6)-carboxyfluorescein acetoxymethyl ester (BCECF) was purchased from Molecular Probes, Inc. (Eugene, OR) and dissolved immediately before use in DMSO (1 mg/ml). A working solution of 2 µg/ml was prepared in Dulbecco's phosphate-buffered saline (PBS) (Gibco). 4',6-diamidino-2-phenylindole (DAPI) was purchased from Sigma Chemical Co. (St. Louis, Mo.). Stock solutions of DAPI were prepared at 100 µg/ml in distilled water by sonication, passed through a 0.45 µm filter, and stored at −20° C. Working solutions of DAPI were prepared at 10 µg/ml in PBS containing 0.5% nonidet P-40 (NP-40) (Sigma). XTT was prepared at a concentration of 1 mg/ml in serum-free RPMI 1640. Phenazine methosulfate (PMS) (Sigma) was prepared at 0.153 mg/ml in PBS and stored at −20° C. Immediately before use, XTT was dissolved at 37° C., and PMS was added to yield a final concentration of 20 µM.

Protocol for Definitive Anti-HIV Evaluations

The appropriate amounts of the pure compounds for anti-HIV evaluations were dissolved in 100% dimethylsulfoxide (DMSO) and then diluted in complete medium to the desired initial concentration (with final DMSO content not exceeding 1%). All serial dilutions of the michellamines A, B, and C, reagent additions, and plate-to-plate transfers were carried out using an automated Biomek 1000 Workstation (Beckman Instruments, Palo Alto, Calif.). Each compound was diluted initially in complete medium and added to a single column of a 96-well microtiter plate (dilution plate). The Biomek was used to perform eight serial dilutions of each drug and to transfer a 100 µl aliquot of each dilution to the test plate. Unexposed CEM-SS or MT-2 cells were plated at a density of $1 \times 10^4$ cells in 50 µl of complete medium. Diluted HIV-1 or HIV-2 virus was then added to appropriate wells in a volume of 50 µl to yield a multiplicity of infection of 0.6. Appropriate cell, virus, and drug controls were used, with the final volume in each well being 200 µl. Uninfected, untreated cell controls, and untreated virus infected cell controls were placed on both sides of the 96-well test plates; drug blanks were placed along the top and bottom of the plates. Cells that received test compounds were included in quadruplicate virus-infected wells and duplicate uninfected wells. Plates were incubated at 37° C. in an atmosphere containing 5% $CO_2$ for 6 days. Subsequently, aliquots of cell-free supernatant were removed from each well using the Biomek, and analyzed for reverse transcriptase activity, p24 antigen production, and synthesis of infectious virions (see further below). A 25 µl sample of 0.002% (w/v) Fluoricon reference particles (590/620 nm) (Baxter Healthcare Corp.) was added to each well of the test plate to be used as an internal standard for fluorescence assays. The Biomek was used to disperse evenly the contents of each well of the test plate and transfer 50 µl aliquots to each of two new microtiter plates. These plates subsequently were used to measure either cellular viability using BCECF or total DNA content using DAPI.

XTT Assay

As an estimate of cellular viability, the metabolic reduction of the tetrazolium salt, XTT, to the soluble, colored formazan was carried out by adding 50 µl of the XTT/PMS solution to each well of the original test plate and incubating for 4 hrs at 37° C. After incubation the plates were covered with adhesive plate sealers (Dynatech, Alexandria, Va.) and shaken, and optical densities were determined using a V-max photometer (Molecular Devices, Inc., Menlo Park, Calif.) at a test wavelength of 450 nm.

BCECF Assay

Cellular viability also was measured using BCECF. Freshly prepared BCECF solution (25 µl) was added to each well of the microtiter plate, and the plates incubated at 37° C. for 30 min. Subsequently, 25 µl of a 2% solution of paraformaldehyde was added to each well and incubated a further 30 min to inactivate the virus. The contents of each well were mixed, and a 75 µl aliquot was then transferred to a filter-bottomed, 96-well plate (Baxter Healthcare Corp.). The plate was placed in the Screen Machine programmed to execute the following protocol: (1) add 20 µl of 0.25% w/v suspension of 3.2 µm polystyrene beads (Baxter Healthcare Corp.) in PBS as a filtration support matrix; (2) filter away the liquid phase using a vacuum pressure of 15 mm Hg for 1½ min; (3) wash the cell-bead cake in each well with PBS using a vacuum pressure of 20 mm Hg for 1 min; and (4) read fluorescence of each well (signal channel=excitation at 485 nm, emission at 535 nm, and reference channel=excitation at 590 nm, emission at 620 nm).

DAPI Assay

Total DNA content of each well was determined by the following modifications to the method described in McCaffrey et al., *In Vitro Cell. Develop. Biol.*, 24, 247–252 (1988). The contents of each well were fixed by adding 25 µl of a 2% paraformaldehyde solution and incubating the plate at 37° C. for 30 min. 25 µl of the DAPI/NP-40 solution was added to each well and incubated for 2 hrs. The contents of each well were mixed, and a 75 µl aliquot was transferred to a filter-bottomed 96-well plate (Baxter Healthcare Corp.). The DAPI plate was placed in the Screen Machine and processed by the same protocol as the BCECF plate above with the signal channel set at an excitation of 400 nm and an emission of 450 nm.

p24 Assay

The production of the HIV-1 internal core p24 antigen was measured using a p24 antigen-capture assay (Coulter Immunology, Hialeah, Fla.). Supernatants from test plates were diluted 1:100 in 10% Triton X-100 and stored frozen at −20° C. until needed. Two hundred microliter aliquots of Triton X-treated samples were added to microtiter wells previously coated with a murine monoclonal anti-HIV-1 p24 antigen. The plates were sealed and incubated at 37° C. for 1 hr. Plate washings were carried out using an automated Denley Wellwash 4 (Coulter Immunology) plate washer. After washing and blotting dry the plates, 200 μl of a biotinylated human monoclonal anti-HIV-1 p24 was added to appropriate wells, and the plates were reincubated for 1 hr at 37° C. After additional washing, 200 μl of a streptavidin-horseradish peroxidase solution was added, and the plates were then incubated for 30 min at 37° C. A tetramethylbenzene solution was added to each well and incubated at room temperature for 30 min. Following incubation, an acidic stopping reagent was added to each well, and the absorbance-was read at 450 nm within 30 min using a Vmax photometer (Molecular Devices). The concentration of p24 was determined by comparison with a standard curve of known p24 concentrations.

Syncytium Assay

The syncytium assay described in Nara et al., *AIDS Res. Hum. Retroviruses*, 3, 283–302 (1987), was used for quantitation of infectious virus. Supernatants from test plates were examined in CEM-SS cell monolayers at multiple dilutions to obtain countable numbers syncytia (50–200 per well) in 2–4 days.

Reverse Transcriptase Assay

A 30 μl aliquot of supernatant was added to 30 μl of a virus disruption buffer containing 50 mM Tris pH 7.8, 0.15 mg/ml dithiothreitol (DTT), and 0.1% Triton X-100. A 10 μl sample of lysed virus was added to 30 μl of a cocktail containing 2 μl of 1M Tris, pH 7.8, 1 μl of 3M KCl, 5 μl of 3 mg/ml DTT, 5 μl of 0.1M magnesium acetate, 10 μl of Poly(rA)·p(dT)$_{10}$ (2 units/ml) (Pharmacia, Piscataway, N.J.), 6.5 μl of distilled H$_2$O, 0.5 μl of 10% Triton X-100, and 10 μl of [$^3$H]dTTP (16.56 Ci/mmol) (Amersham Corp., Arlington Heights, Ill.). Samples were incubated for 30 min at 37° C., harvested onto DE81 ion exchange paper, and allowed to absorb for 15 min. Sample pads first were rinsed six times with 5% Na$_2$HPO$_4$, then twice with distilled H$_2$O. Pads were dried and counted in a liquid scintillation counter. Samples were counted in triplicate.

Linearity of Assay Endpoint to Cell Number

Exponentially-growing CEM-SS cells were harvested, washed and plated in 96-well microtiter wells at varying cell concentrations. Following the cell inoculation, the cells were treated with either XTT, BCECF, or DAPI according to the above protocols. The fluorescence assays, using BCECF and DAPI, showed excellent linearity over a wide range of cell concentrations. Reproducible results could be obtained from both assays with cell numbers below 1000 cells/assay. The colorimetric XTT assay also showed good linearity but with a higher detection limit of 5,000–10,000 cells/assay.

Antiviral Activity of the Michellamines

FIGS. 2 and 3 illustrate the antiviral activity of michellamine A, as the free base or the HBr salt, respectively. FIGS. 4 and 5 illustrate the antiviral activity of michellamine B, as the free base or the HBr salt, respectively. Both compounds gave very similar activity profiles.

FIGS. 2A and 2C, 3A and 3C, 4A and 4C, and 5A and 5C describe the relative numbers of viable human CEM-SS lymphoblastoid target cells, either uninfected (o) or infected (●) with the HIV-1 virus, remaining in the culture wells 6 days after introduction of a range of concentrations of michellamines in the form of their free bases or their HBr salts. The results are represented as the percent of the appropriate uninfected, non-drug treated controls. At michellamine concentrations between approximately 20 to 200 μM, both the BCECF and the XTT viability assays showed essentially complete protection of the target cells from the killing effects of the virus. There was little or no direct cytotoxicity of the michellamines to the target cells with drug concentrations below approximately 100 μM. The results of the DNA assay (FIGS. 2B, 3B, 4B, and 5B) were consistent with the viability assays, i.e., the results provided further indication of the antiviral activity of the michellamines. The DNA measurements, as expected, paralleled the cell numbers present.

FIGS. 2D, 3D, 4D, and 5D show indices of viral replication in cultures of human CEM-SS lymphoblastoid target cells infected with HIV-1 and assayed 6 days after introduction of various concentrations of michellamines in the form of their free bases or HBr salts. The results are represented as the percent of the appropriate HIV-infected, non-drug treated controls. At michellamine concentrations within the same range giving essentially complete cytoprotection (see above), there was a dramatic, essentially complete inhibition of p24 viral core antigen production (▲) and viral reverse transcriptase activity (■), which are indicators of viral replication; there was a similarly complete inhibition of SFU, further indicating a loss of infectious virus.

In another study, the acetate salts of michellamines A, B, and C were evaluated in a side-by-side comparison for anti-HIV-1 activity using the XTT assay. The results are summarized in Table 4. All three compounds exhibited similar anti-HIV-1 activity.

TABLE 4

| RESULTS OF COMPARISON STUDY OF ANTI-HIV-1 ACTIVITY OF MICHELLAMINES A, B, and C | | |
|---|---|---|
| Michellamine | EC$_{50}$ (μM) | IC$_{50}$ (μM) |
| A | 9.6 | 168 |
| B | 9.6 | >240 |
| C | 12.8 | 193 |

In vitro cytoprotective effects such as the above are known to predict for antiviral activity in humans. For example, AZT similarly was selected initially for evaluation in human patients on the basis of its in vitro cytoprotective effects against the HIV-1 form of the AIDS virus in cultured human lymphoblastoid cell lines (Yarchoan et al., *Lancet*, 1, 575–580 (1986)).

Figure 6A:
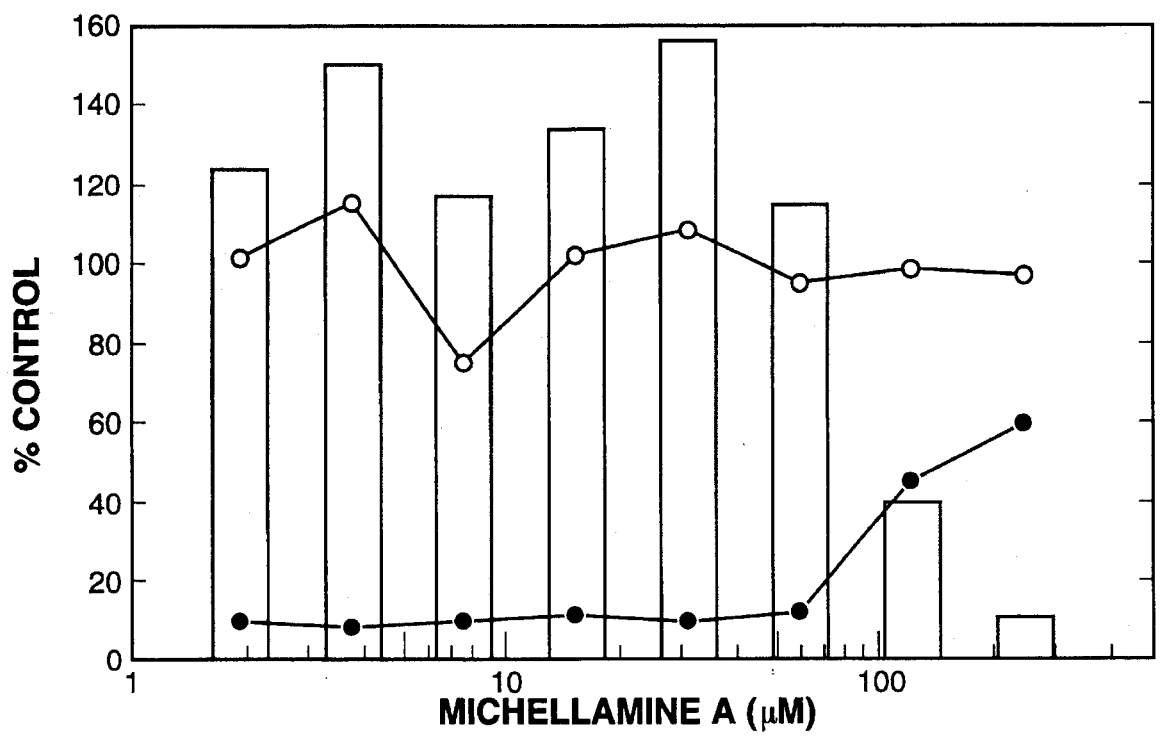
FIGS. 6A and 6B show the anti-HIV-2 activity of michellamine A (free base and HBr salt).
Figure 6B:
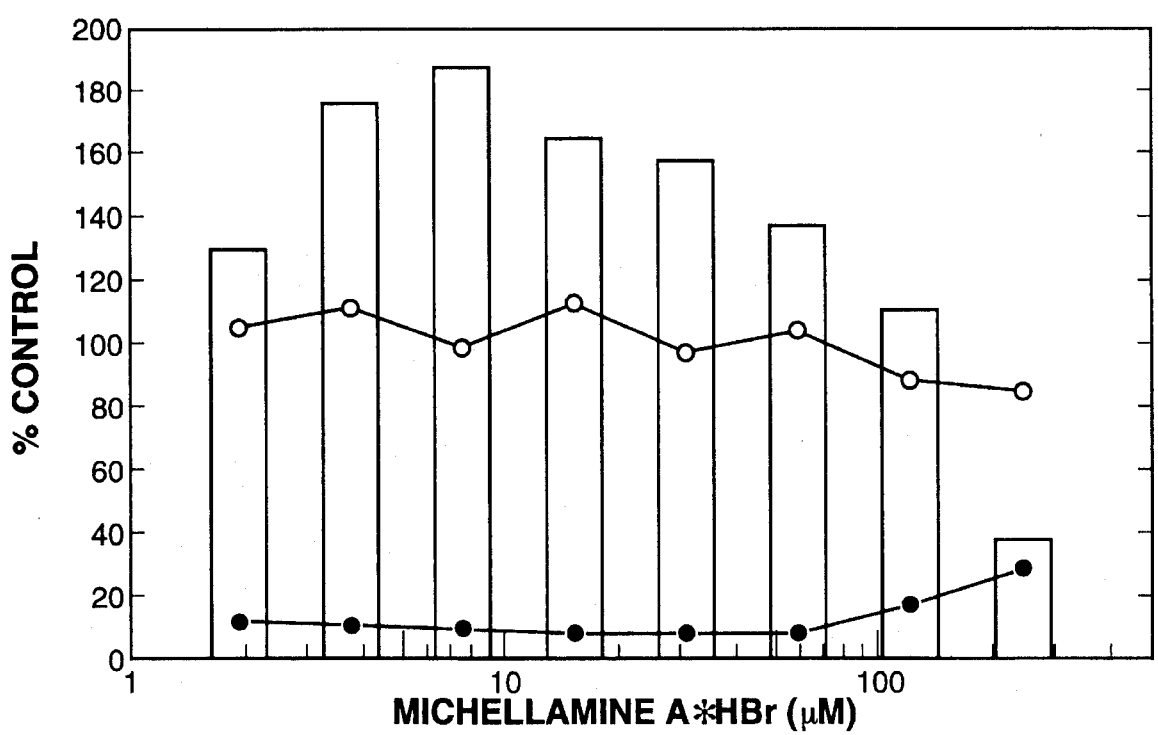
Figure 7A:
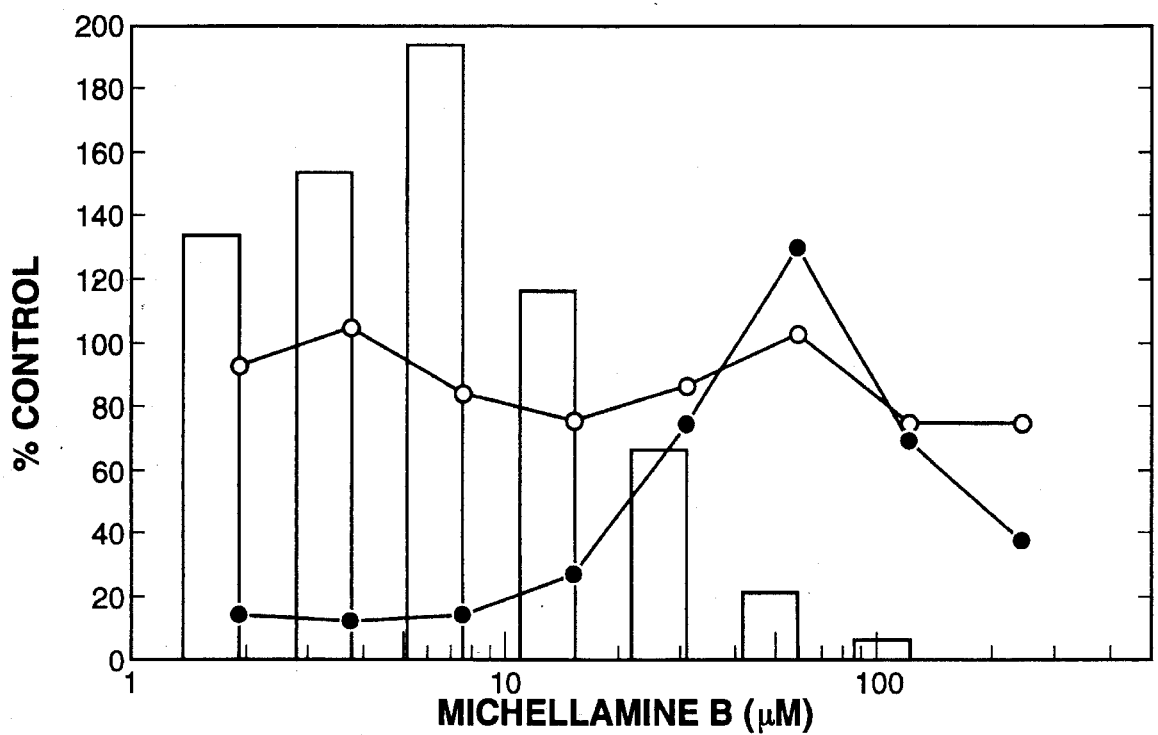
FIGS. 7A and 7B show the anti-HIV-2 activity of michellamine B (free base and HBr salt).
Figure 7B:
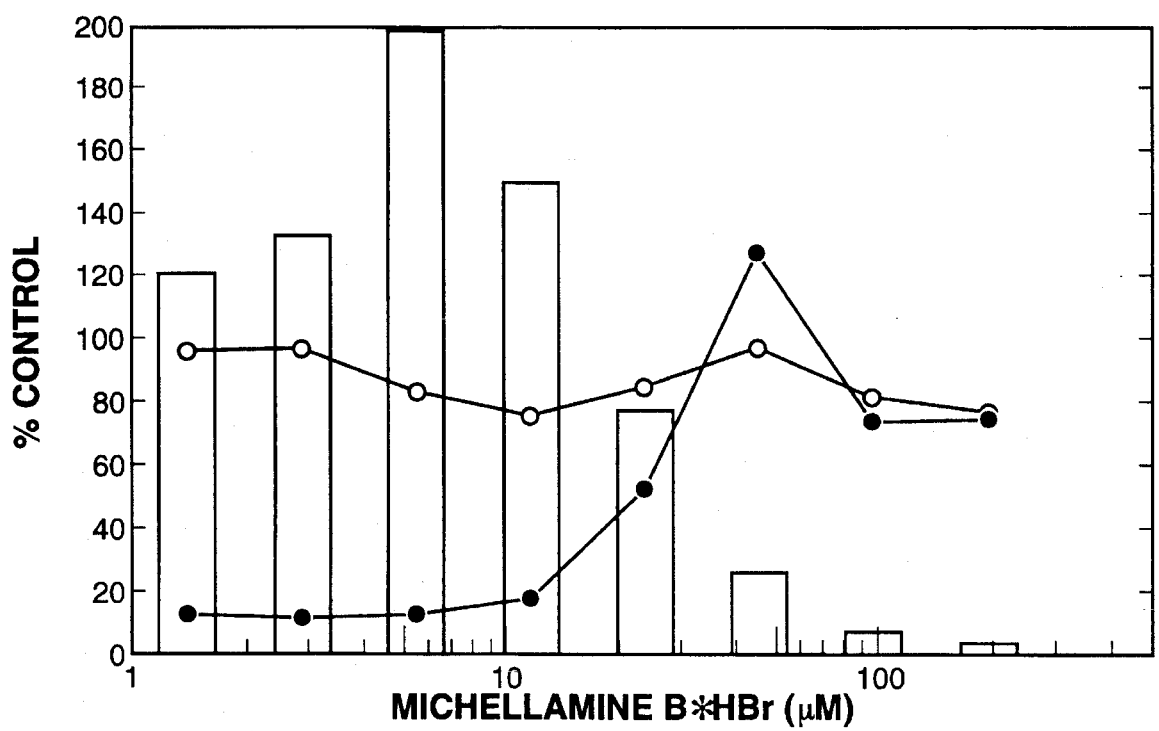

FIG. 6 describes the relative numbers of viable human lymphoblastoid MT-2 cells, either uninfected (o) or infected with the NIH-DZ strain of the HIV-2 virus (●), remaining in the culture wells 6 days after introduction of a range of concentrations of michellamine A in the form of its free base (FIG. 6A) or in the form of its HBr salt (FIG. 6B). FIG. 7 describes the relative numbers of viable human lymphoblastoid MT-2 cells, either uninfected (o) or infected with the NIH-DZ strain of the HIV-2 virus (●), remaining in the culture wells 6 days after introduction of a range of concentrations of michellamine B in the form of its free base (FIG. 6A) or its HBr salt (FIG. 6B). The results are represented both in FIG. 6 and in FIG. 7 as the percent of the appropriate controls. Both michellamines A and B, either as their free bases or as their HBr salts, showed antiviral effects (FIGS. 6 and 7) against HIV-2. However, michellamine B consistently was more potent than michellamine A against HIV-2. With concentrations of michellamine B typically between 30–100 μM, essentially complete protection was obtained against the killing effects of HIV-2 upon MT-2 cells. In contrast, with concentrations of michellamine A as high as 250 μM there was only partial protection (20–40%) of the MT-2 cells against HIV-2.

Figure 8A:
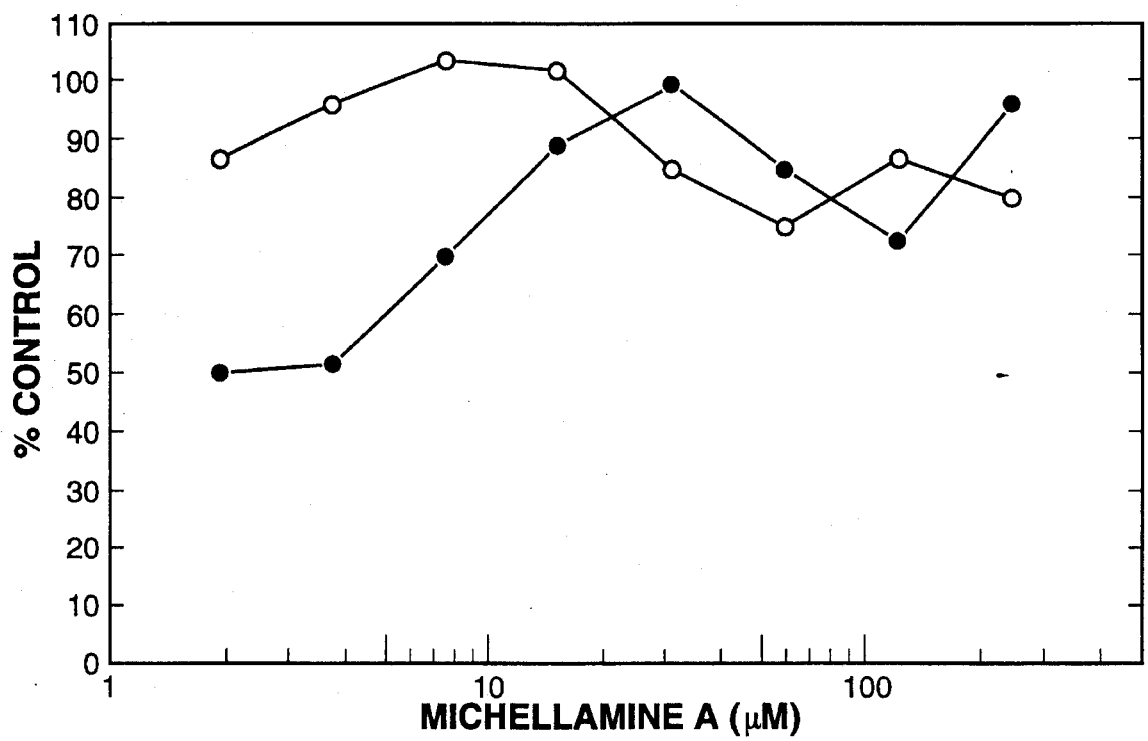
FIGS. 8A, 8B, and 8C show the XTT anti-HIV assay results of comparative testing of the acetate salts of michellamines A, B, and C, respectively, upon uninfected (o) CEM-SS cells and upon CEM-SS cells infected (●) with the CBL20 strain of HIV-2. The horizontal axis scaling units are μM, and the data points are represented as the percent of the uninfected, non-drug treated control values.
Figure 8B:
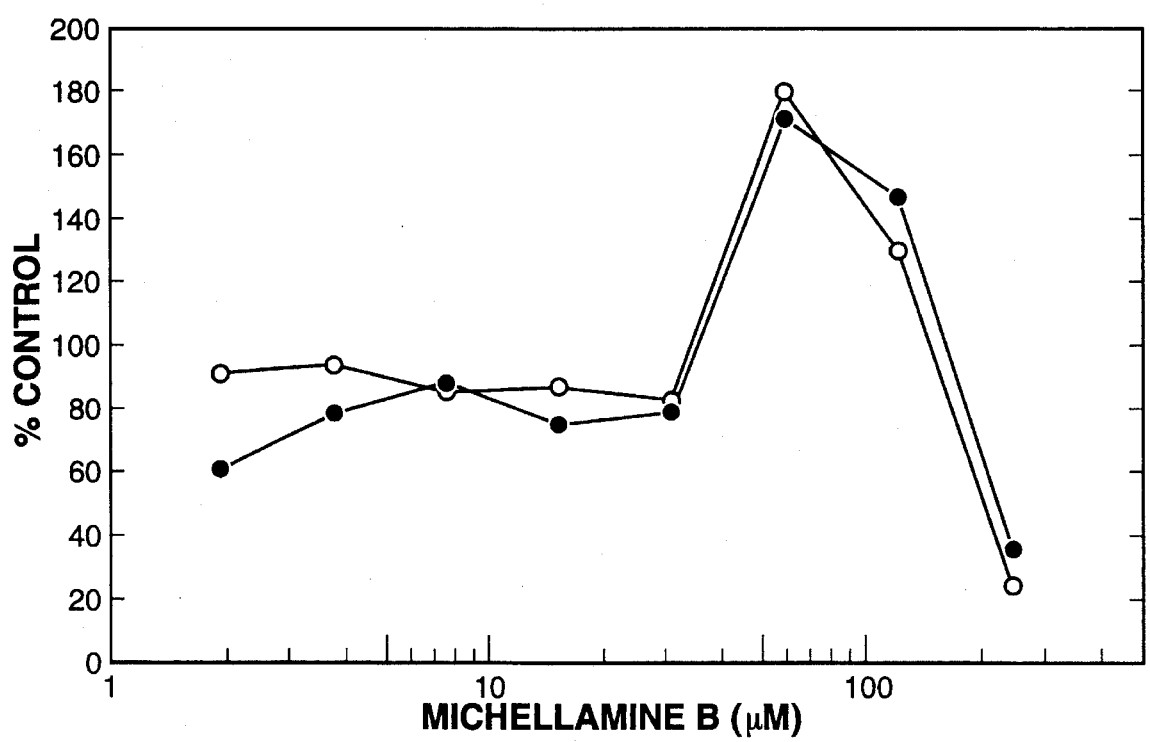
Figure 8C:
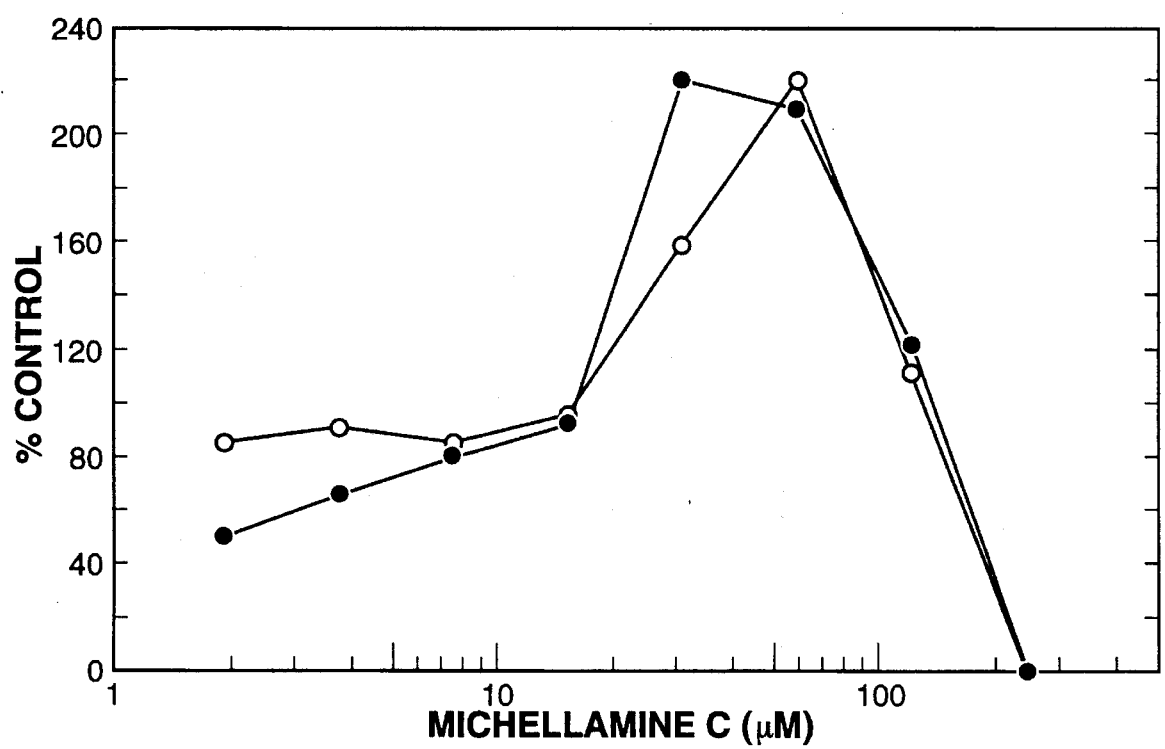

A side-by-side comparative analysis was performed of the anti-HIV-2 activities of the acetate salts of michellamines A, B, and C using the CBL20 strain of HIV-2 with CEM-SS target cells and the XTT assay. FIGS. 8A, 8B, and 8C show the results for various concentrations of michellamines A, B, and C, respectively, tested against uninfected (o) cells and upon cells infected (●) with the HIV-2. In this study, michellamines B and C showed similar potencies against HIV-2 ($EC_{50} < 2$ μM), while michellamine A appeared somewhat less potent ($EC_{50} \sim 10$ μM).

As described above, the michellamines inhibit at least two types of HIV retrovirus. As one skilled in the art will appreciate, the michellamines and compositions thereof will likely inhibit other retroviruses and other pathogenic viruses.

Example 7

This example illustrates various possible pharmaceutical compositions which include the compounds of the present invention.

The compounds of the present invention may be made into pharmaceutical compositions by combination with appropriate, pharmaceutically acceptable carriers or diluents, and may be formulated into preparations in solid, semi-solid, liquid, or gaseous forms such as tablets, capsules, powders, granules, ointments, solutions, suppositories, injections, inhalants, and aerosols in the usual ways for their respective route of administration.

The compounds can be used singularly alone, in combination with each other, or in combination with other antiviral agents. When patients infected with HIV-1 and/or HIV-2 are being treated, at least one compound of the present invention can be co-administered with AZT.

The following methods and excipients are merely exemplary and are in no way limiting.

In pharmaceutical dosage forms, the compounds of the present invention may be used in the form of their pharmaceutically acceptable salts and also may be used alone or in appropriate association, as well as in combination, with other pharmaceutically active compounds.

In the case of oral preparations, the compounds of the present invention may be used alone or in combination with appropriate additives to make tablets, powders, granules, or capsules, e.g., with conventional additives such as lactose, mannitol, corn starch, or potato starch; with binders such as crystalline cellulose, cellulose derivatives, acacia, corn starch, or gelatins; with disintegrators such as corn starch, potato starch, or sodium carboxymethylcellulose; with lubricants such as talc or magnesium stearate; and, if desired, with diluents, buffering agents, moistening agents, preservatives, and flavoring agents.

The compounds of the present invention may be formulated into preparations for injections by dissolving, suspending, or emulsifying them in an aqueous or nonaqueous solvent, such as vegetable or other similar oils, synthetic aliphatic acid glycerides, esters of higher aliphatic acids, or propylene glycol; and, if desired, with conventional additives such as solubilizers, isotonic agents, suspending agents, emulsifying agents, stabilizers, and preservatives.

The compounds of the present invention can be utilized in aerosol formulation to be administered via inhalation. The compounds of the present invention can be formulated into pressurized acceptable propellants such as dichlorodifluoromethane, propane, nitrogen, and the like.

Furthermore, the compounds of the present invention may be made into suppositories by mixing with a variety of bases such as emulsifying bases or water-soluble bases. The compounds of the present invention can be administered rectally via a suppository. The suppository can include vehicles such as cocoa butter, carbowaxes, and polyethylene glycols, which melt at body temperature, yet are solid at room temperature.

Unit dosage forms for oral or rectal administration such as syrups, elixirs, and suspensions may be provided wherein each dosage unit, e.g., teaspoonful, tablespoonful, tablet, or suppository contains a predetermined amount of the composition containing at least one compound of the present invention; similarly, unit dosage forms for injection or intravenous administration may comprise a michellamine composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of at least one compound of the present invention calculated in an amount sufficient to produce the desired effect in association with a pharmaceutically acceptable, diluent, carrier, or vehicle. The specifications for the novel unit dosage forms of the present invention depend on the particular compound employed and the effect to be achieved, as well as the pharmacodynamics associated with each compound in the host.

The pharmaceutically acceptable excipients, for example, vehicles, adjuvants, carriers, or diluents, are readily available to the public.

One skilled in the art can determine easily the appropriate method of administration for the precise formulation of the composition being used. Any necessary adjustments in dose can be made readily to meet the nature or severity of the infection and adjusted accordingly by the skilled practitioner.

Example 8

This example illustrates various possible uses of the michellamines of the present invention in the treatment of viral infections.

The present invention relates further to a method of treating viral infections comprising the administration of an antiviral effective amount of at least one compound of the present invention. Antiviral effective amount is defined as that amount of compound required to be administered to an individual patient to achieve an antiviral effective blood and/or tissue level to inhibit the virus. The antiviral effective blood level might be chosen, for example, to inhibit a virus in a screening assay. An example of such an amount would be 20–200 μM, e.g., from FIGS. 2–7. Alternatively, the antiviral effective blood level can also be defined as that concentration which inhibits markers (e.g., p24) of the virus in the patient's blood, or which renders the patient asymptomatic to the particular viral infection. Since a fixed antiviral effective blood level is used as the preferred endpoint for dosing, the actual dose and schedule for drug administration for each patient will vary depending upon interindividual differences in pharmacokinetics, drug disposition, and metabolism. Moreover, the dose may vary when the compounds are used prophylactically or when used in combination with other drugs.

Such dosage amounts can be readily ascertained without undue burden and experimentation by those skilled in the art.

As an example of an antiviral effective amount, the dosage for humans can range from about between 0.01 mg/kg body weight to 200 mg/kg body weight.

All of the references cited herein are hereby incorporated in their entireties by reference.

While this invention has been described with an emphasis upon preferred embodiments, it will be obvious to those of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A isolated and purified compound having the formula:

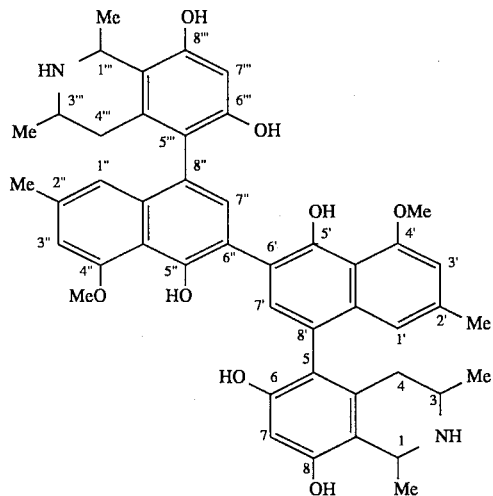

or a pharmacologically acceptable salt thereof.

2. The compound of claim 1 having the formula:

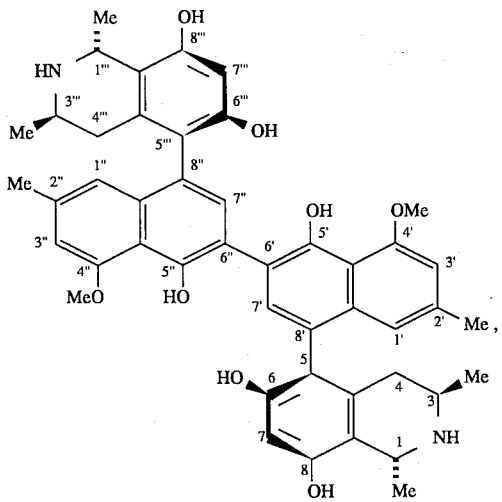

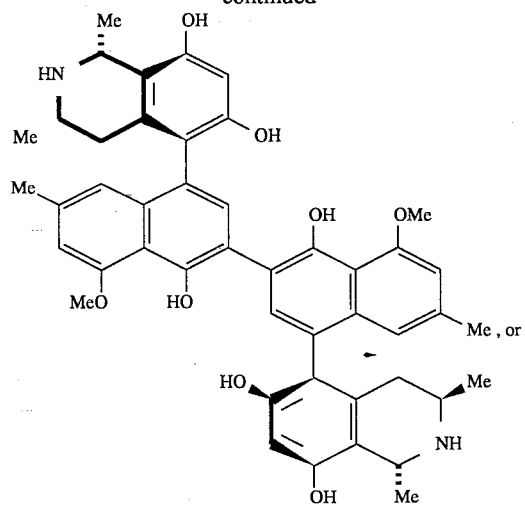

or a pharmacologically acceptable salt thereof.

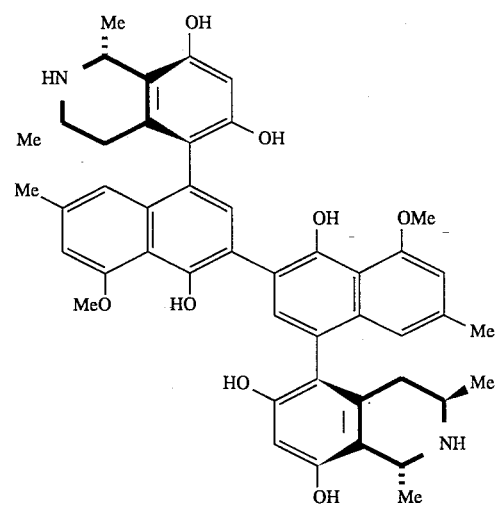

or a pharmacologically acceptable salt thereof.

3. An isolated and purified compound having the formula:

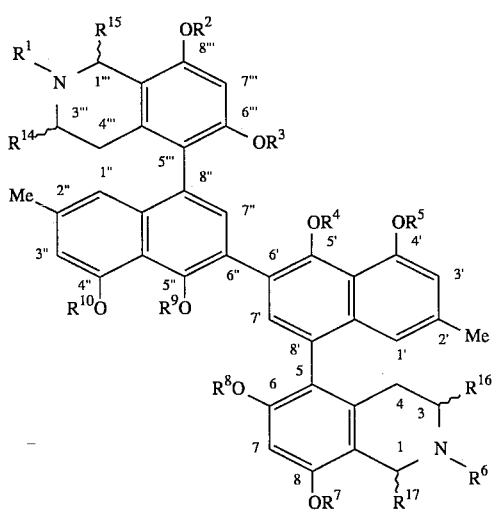

or a pharmacologically acceptable salt thereof, wherein $R^1$ and $R^6$ are the same or different and are each H, $C_1$–$C_6$ alkyl, $R^{11}CO$— or $R^{11}SO_2$— wherein $R^{11}$ is $C_1$–$C_6$ alkyl or aryl;

$R^2$, $R^3$, $R^4$, $R^7$, $R^8$ and $R^9$ are the same or different and are each H, $C_1$–$C_6$ alkyl, $R^{11}CO$—, $R^{11}SO_2$— wherein $R^{11}$ is defined above;

$R^5$ and $R^{10}$ are the same or different and are each H, $C_1$–$C_6$ alkyl,

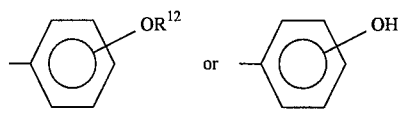

wherein $R^{12}$ is $C_1$–$C_6$ alkyl or $R^{13}CO$— or $R^{13}SO_2$—, wherein $R^{13}$ is $C_1$–$C_6$ alkyl or aryl; $R^{14}$, $R^{15}$, $R^{16}$ and $R^{17}$ are the same or different and are each ◂CH₃ or ⋯CH₃;

and wherein one or more of the ring H positions at 1', 3', 7', 4, 7, 1", 3", 7", 4''' and 7''' can be substituted with a halogen, nitro, amino, hydroxyl, thiol or cyano group.

4. The compound of claim 3 having the formula:

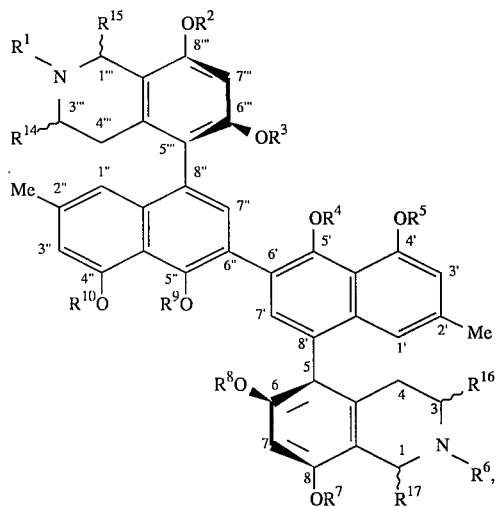

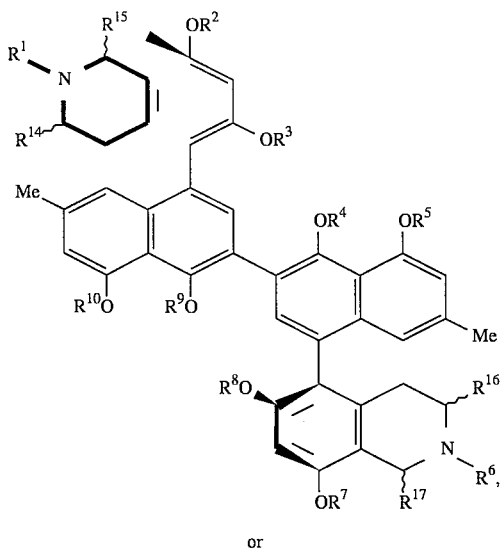

or

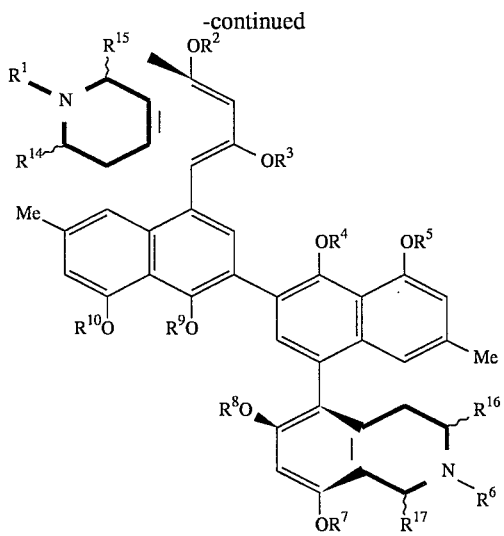

wherein $R^1$ and $R^6$ are the same or different and are each H, $C_1$–$C_6$ alkyl, $R^{11}CO$—, or $R^{11}SO_2$— wherein $R^{11}$ is $C_1$–$C_6$ alkyl or aryl;

$R^2$, $R^3$, $R^4$, $R^7$, $R^8$ and $R^9$ are the same or different and are each H, $C_1$–$C_6$ alkyl, $R^{11}CO$—, $R^{11}SO_2$— wherein $R^{11}$ is defined above;

$R^5$ and $R^{10}$ are the same or different and are each H, $C_1$–$C_6$ alkyl,

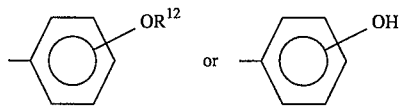

wherein $R^{12}$ is $C_1$–$C_6$ alkyl or $R^{13}CO$— or $R^{13}SO_2$—, wherein $R^{13}$ is $C_1$–$C_6$ alkyl or aryl; $R^{14}$, $R^{15}$, $R^{16}$ and $R^{17}$ are the same or different and are each ◂CH₃ or ⋯CH₃;

and wherein one or more of the ring H positions at 1', 3', 7', 4, 7, 1", 3", 7", 4''' and 7''' can be substituted with a halogen, nitro, amino, hydroxyl, thiol or cyano group, or a pharmacologically acceptable salt thereof.

5. An antiviral composition which comprises an antiviral effective amount of at least one compound according to claim 1 and a pharmacologically acceptable carrier.

6. An antiviral composition which comprises an antiviral effective amount of at least one compound according to claim 2 and a pharmaceutically acceptable carrier.

7. An antiviral composition which comprises an antiviral effective amount of at least one compound according to claim 3 and a pharmacologically acceptable carrier.

8. An antiviral composition which comprises an antiviral effective amount of at least one compound according to claim 4 and a pharmacologically acceptable carrier.

9. The composition according to claim 5, further comprising an antiviral effective amount of AZT or other known effective antiviral agent.

10. The composition according to claim 6, further comprising an antiviral effective amount of AZT or other known effective antiviral agent.

11. The composition according to claim 7, further comprising an antiviral effective amount of AZT or other known effective antiviral agent.

12. The composition according to claim 8, further comprising an antiviral effective amount of AZT or other known effective antiviral agent.

13. A method of inhibiting replication of a virus within a cell which comprises contacting said cell with an antiviral effective amount of at least one compound according to claim 1.

14. The method of claim 13, which further comprises contacting said cell with an antiviral effective amount of AZT.

15. The method of claim 13, wherein said virus is a retrovirus.

16. The method of claim 15, wherein said retrovirus is a human immunodeficiency virus.

17. The method of claim 13, wherein said human immunodeficiency virus is selected from the group consisting of HIV-1 and HIV-2.

18. The method of claim 13, wherein said contacting is done in vitro.

19. A method of inhibiting replication of a virus within a cell which comprises contacting said cell with an antiviral effective amount of at least one compound according to claim 3.

20. The method of claim 19, which further comprises contacting said cell with an antiviral effective amount of AZT.

21. The method of claim 19, wherein said virus is a retrovirus.

22. The method of claim 19, wherein said retrovirus is a human immunodeficiency virus.

23. The method of claim 19, wherein said human immunodeficiency virus is selected from the group consisting of HIV-1 and HIV-2.

24. The method of claim 19, wherein said contacting is done in vitro.

25. A method of inhibiting replication of a virus within a cell which comprises contacting said cell with an antiviral effective amount of at least one compound according to claim 2.

26. The method of claim 25, which further comprises contacting said cell with an antiviral effective amount of AZT.

27. The method of claim 25, wherein said virus is a retrovirus.

28. The method of claim 25, wherein said retrovirus is a human immunodeficiency virus.

29. The method of claim 25, wherein said human immunodeficiency virus is selected from the group consisting of HIV-1 and HIV-2.

30. The method of claim 25, wherein said contacting is done in vitro.

31. A method of inhibiting replication of a virus within a cell which comprises contacting said cell with an antiviral effective amount of at least one compound according to claim 4.

32. The method of claim 31, which further comprises contacting said cell with an antiviral effective amount of AZT.

33. The method of claim 31, wherein said virus is a retrovirus.

34. The method of claim 31, wherein said retrovirus is a human immunodeficiency virus.

35. The method of claim 31, wherein said human immunodeficiency virus is selected from the group consisting of HIV-1 and HIV-2.

36. The method of claim 31, wherein said contacting is done in vitro.

* * * * *

UNITED STATES PATENT AND TRADEMARK OFFICE
CERTIFICATE OF CORRECTION

PATENT NO. : 5,455,251
DATED : October 3, 1995
INVENTOR(S) : Boyd et al.

It is certified that error appears in the above-indentified patent and that said Letters Patent is hereby corrected as shown below:

On the title page item [75], Johnson Jato's residence is listed as "Cambodia" but should read --Cameroon--.

Signed and Sealed this

Fifth Day of March, 1996

Attest:

BRUCE LEHMAN

*Attesting Officer*  *Commissioner of Patents and Trademarks*